United States Patent [19]

Lai et al.

[11] Patent Number: 4,722,806
[45] Date of Patent: Feb. 2, 1988

[54] ALKYLATED POLYALKYLENEPOLYAMINES, SUBSTITUTED OXO-PIPERAZINYL-TRIAZINES AND UV LIGHT STABILIZED COMPOSITIONS

[75] Inventors: John T. Lai, Broadview Heights; Pyong N. Son, Akron, both of Ohio

[73] Assignee: The B. F. Goodrich Company

[21] Appl. No.: 721,270

[22] Filed: Apr. 9, 1985

Related U.S. Application Data

[63] Continuation-in-part of Ser. No. 664,901, Oct. 26, 1984, Pat. No. 4,547,538, which is a continuation-in-part of Ser. No. 350,536, Feb. 2, 1982, Pat. No. 4,480,092.

[51] Int. Cl.$^4$ .............................. C09K 15/22
[52] U.S. Cl. .................... 252/403; 252/404; 524/101; 524/323; 524/335; 525/417
[58] Field of Search ............. 252/600, 404, 589, 403; 524/100, 101, 323, 335; 525/417

[56] References Cited

U.S. PATENT DOCUMENTS

| | | | |
|---|---|---|---|
| 3,397,205 | 8/1968 | Juethi et al. | 252/589 |
| 4,028,331 | 6/1977 | Hotta et al. | 252/404 |
| 4,110,304 | 8/1978 | Gilg et al. | 252/404 |
| 4,547,538 | 10/1985 | Lai | 524/100 |

Primary Examiner—Edward J. Smith
Assistant Examiner—Peter F. Kulkosky
Attorney, Agent, or Firm—Alfred D. Lobo; Alan A. Csontos

[57] ABSTRACT

A branched chain polyalkylenepolyamine ("PAPA") amine having plural amine groups including a secondary amine group intermediate terminal primary amine groups and having at least two carbon atoms between each amine group, is reductively alkylated with a ketone to provide a PAPA alkylated only at an unhindered primary amine group. A preselected degree of steric hindrance at amine groups near each end of the chain enables cyclization by the 'ketoform synthesis' by reaction with a ketone in such a manner as to form a polysubstituted piperazinone ("PSP") ring which includes N atoms of proximate primary and secondary amine groups of the alkylated PAPA. The PSP so formed may then be reacted with a reactive triazine ring so that a PSP substituent is linked to the triazine ring through a single N atom and at least two C atoms, to form a 2-oxo-piperazinyl-triazine ("PIP-T"). Oligomers of the PIP-T may be prepared. The PIP-T compounds are excellent stabilizers against ultraviolet (uv) light degradation in light-sensitive synthetic resinous materials. In combination with particular hindered phenols PIP-T compounds are found to provide better antioxidant properties than that obtained as the theoretical additive effect of the PIP-T and the hindered phenol, separately.

12 Claims, No Drawings

ALKYLATED POLYALKYLENEPOLYAMINES, SUBSTITUTED OXO-PIPERAZINYL-TRIAZINES AND UV LIGHT STABILIZED COMPOSITIONS

CROSS-REFERENCE TO RELATED APPLICATIONS

This application is a continuation-in-part of Ser. No. 664,901 filed Oct. 26, 1984, now U.S. Pat. No. 4,547,538 which is, in turn, a continuation-in-part application of Ser. No. 350,536 filed Feb. 2, 1982, now issued as U.S. Pat. No. 4,480,092.

BACKGROUND OF THE INVENTION

Organic materials, whether natural or synthetic, are conventionally protected against degradation by ultraviolet (UV) light by incorporating a UV light stabilizer in the material. Many classes of compounds are known to be useful UV light stabilizers, some being more effective than others. Particularly effective 2-keto-diazacycloalkanes which provide stabilized compositions resistant to degradation by UV light, include the 2-keto-1,4-diazacycloalkanes disclosed in U.S. Pat. No. 4,190,571; and, the 2-keto-1,5-diazacycloalkanes disclosed in U.S. Pat. No. 4,207,228. Other 2-keto-diazacycloalkanes useful as UV light stabilizers are disclosed in U.S. Pat. Nos. 3,919,234; 3,920,659; and 3,928,330 which teach substituted piperazinediones. Cycloalkanes useful as UV light stabilizers are disclosed in Ger. Offen. 2,315,042; Japanese Pat. Nos. 7,453,571 and 7,453,572.

The compounds of this invention belong to a well-recognized chemical class of ultraviolet light stabilizers. They are multi-ringed triazine derivatives. Compounds of this class include piperidinyl-triazine derivatives such as are disclosed in U.S. Pat. No. 4,263,434 (hereafter "434" for brevity) and French Pat. No. 2181 059, each of which describe the preparation of monoaza ring substituents linked to a triazine ring, and teach the particular use of these derivatives as light stabilizers in polyolefins.

However, the compounds of the French patent are known to have poor resistance to extraction with an aqueous solvent which appears to be a characteristic of this class of compounds. The compounds of the '434 patent are known to have overcome, for the most part, such a disadvantage, presumably because of the particular linking of the piperidinyl substituents to the triazine ring. In addition to the different linking groups, compared with those of the French compounds, the '434 compounds include a single piperazine ring substituent, not part of a repeating unit, which is directly bonded to the triazine ring, that is, without any linking groups. Moreover, though substituted piperazinones are known to be effective stabilizers, there is no suggestion that linking such a piperazinone through at least a three-atom chain of one N (nitrogen) atom and at least two C (carbon) atoms to a triazine ring, might impart compositions containing such distally linked piperazinone substituents exceptional properties, including fastness to extraction with aqueous solutions.

The concept of structurally changing the nature of the linking group in multi-ringed triazine derivatives, and changing the structure of rings to which the triazine ring is linked, initiated the search for effective triazine-based compounds. The heretofore unknown effectiveness of (a) reductive alkylation of a branched chain polyalkylenepolyamine ("PAPA") with a ketone, and (b) the ketoform reaction to preferentially cyclize proximate primary and secondary amine groups in alkylated PAPA which contain a sterically tailored hindered primary amine group which is nevertheless reactive, permitted the implementation of the concept. Testing the compounds as stabilizers in various synthetic resins, and particularly in polyolefins, proved that a substituted piperazinone linked to a triazine ring through one N atom and at least two C atoms (hence "distally linked"), yields effective stabilizers.

The present invention is particularly directed to (a) novel alkylated PAPA, (b) a novel synthesis for the alkylated PAPA, (c) novel uv light stabilizers classed as hindered amine-triazines, more specifically 2-oxo-piperazinyl-triazine ("PIP-T") derivatives, (d) novel syntheses for the PIP-T derivatives, and (e) novel compositions in which 2-oxo-piperazinyl-triazine derivatives are incorporated. The novel PIP-T compounds have at least one substituted piperazinone substituent which is distally linked to a triazine ring, and when, in addition, a piperidinyl, piperazinyl or other substituent is directly linked to the triazine ring, the piperidinyl, piperazinyl or other substituent may become part of a repeating unit. It is to this difference in structure to which the effectiveness of these compounds is attributed.

The reductive alkylation of polyalkylenepolyamines ("PAPA") is well known and described with numerous examples in the chapter entitled "Preparation of Amines by Reductive Alkylation" by W. S. Emerson in *Organic Reactions*, Vol 4, John Wiley & Sons, New York, N.Y. However there is no teaching that reductive alkylation may result in alkylation only at a particular primary amino group to the exclusion of all other amino groups, such result being obtained with a PAPA only by hindering one of the two primary amine groups and reacting with a ketone.

The synthesis of the novel stabilizers of this invention is facilitated by the peculiar action of certain onium salts in an aqueous alkaline medium, which action facilitates the interaction of an amine nucleophilic agent such as a primary or secondary amine, with chloroform or other trichloromethide generating agent, and a ketone or aromatic aldehyde. The organic onium salts of nitrogen, phosphorus and sulfur are well known. They are ionized in aqueous solutions to form stable cations. Certain onium salts have provided the basis for phase transfer catalysis in a wide variety of reactions, a recent and comprehensive review of which is contained in Angewandte Chemie, International Edition in English, 16 493–558 (August 1977). Discussed therein are various anion transfer reactions where the onium salt exchanges its original anion for other anions in the aqueous phase. These ion pairs can then enter a water immiscible, organic liquid phase, making it possible to carry out chemistry there with the transported anion, including OH$^-$ ions. Many reactions involving water immiscible solutions of various simple organic molecules have been described. Though the use of phase transfer catalysts facilitate the cyclization of an appropriately sterically hindered branched chain amine having proximate primary and secondary amine groups amongst plural amine group in the chain, the reaction has also been found to proceed, though relatively slowly, by simply using a large excess of the ketone or aromatic aldehyde either of which is the the essential carbonyl containing compound which contributes the carbonyl group to the 2-position of the diazacycloalkane ring.

A phase transfer catalyzed reaction known as the "ketoform reaction" is disclosed in U.S. Pat. No. 4,167,512, which proceeds by virtue of a phase transfer catalyzed reaction mechanism in which an amine, a haloform and a carbonyl containing ("carbonyl") compound are separate reactants. This reaction is illustrated in one particular example by the reaction of a N,N'-alkyl substituted ethylene diamine with acetone and chloroform; and, in another example, with o-phenylene diamine reacted with cyclohexanone and chloroform. The reaction product in each example is a 2-keto-1,4-diazacycloalkane.

Though both ketones and aldehydes are taught as being effective reactants in the ketoform reaction, it has now been discovered that only ketones are effective in the cyclization of a PAPA. Accordingly, our present invention extends the use of the ketoform reaction to novel alkylated PAPA.

A more detailed teaching of the ketoform synthesis will be found in an article titled "Hindered Amines. Novel Synthesis of 1,3,3,5,5-Pentasubstituted-2-Piperazinones" by John T. Lai in J. Org. Chem. 45, 754 (1980).

It has been found that there is generally a strong antagonistic effect between many a hindered amine light stabilizer ("HALS") and a hindered phenol antioxidant ("AO") used in combination for the stabilization of polymers, as disclosed in "Photostabilizing Performance of a Hindered Piperidine Compound in Polypropylene Film: Antioxidant/Light Stabilizer Effects" by N. S. Allen Polym. Degrad. Stabil. 2, 129 (1980) and "Catalytic Thermal Oxidation of Phenolic Antioxidants by Hindered Piperidine Compounds" by N. S. Allen Polym. Degrad. Stabil., 3, 73 (1980–81).

It has also been found that a particular hindered phenol AO, namely tris(3,5-di-t-butyl-4-hydroxybenzyl)isocyanurate* commercially available as Goodrite ®3114, and a bis(hindered piperidine) photostabilizer ("PS") commercially available as Tinuvin 770, showed an unexpectedly beneficial coaction, as disclosed in "Interaction Between Antioxidants and Hindered Piperidine Compounds in the Photostabilization of Polypropylene: Influence of Processing History" by N. S. Allen et al, Polym. Photochem. 1, 11 (1981).
*also named 1,3,5-tris[(3,5-di-t-butyl-4-hydroxyphenyl)methyl]-1,3,5-triazine-2,4,6-(1H,3H,5H)-trione It was further found that bis-1-(piperazin-2-one) provided not only excellent photostabilization properties as disclosed in U.S. Pat. No. 4,190,571 but also excellent AO properties, as disclosed in U.S. Pat. No. 4,309,336. Moreover, the bis-1-(piperazin-2-one), like many other hindered piperazin-2-one PS compounds, in combination with hindered phenol AOs, were more effective as both PSs and AOs than the sum of their individual effectiveness as PSs and AOs, as disclosed in "Hindered Diazacycloalkanes as UV Stabilizers and Antioxidants" by J. T. Lai et al Polym, Preprints, 25(1), 1984.

Yet, quite surprising is the disclosure that commercially available Chimassorb 944 when used in combination with BHT, Goodrite 3114 and Irganox 1010 is indeed less effective as determined by Weather-O-Meter tests (see brochure entitled "Light Stabilization of Polypropylene Multifilaments and Monofilaments" published by Chimosa S.P.A. (1978), FIG. 3.) combination with hindered phenol AOs generally, it is evident that the effectiveness of any HALS which is structurally dissimilar from the foregoing HALS, can be no more predictable. Certainly, there was no reason to expect that a compound from the particular class of HALS containing linked piperazinone and triazine rings, when combined with one of specific hindered phenols, would exhibit a higher degree of PS and AO activity than that obtained by summing the activity of the individual HALS and hindered phenol when used separately This unique synergistic behavior of a PIP-T compound is now attributable to its being less basic, because of the 2-one group, than compounds containing linked triazine and pyridine, piperidine, or piperazine rings.

SUMMARY OF THE INVENTION

It has been discovered that the reaction of a branched chain polyalkylenepolyamine ("PAPA") having plural amine groups including a secondary amine group intermediate terminal primary amine groups one of which is hindered, and having at least two carbon atoms between each group, may be selectively reductively alkylated with a ketone in an unexpectedly quite different manner from the known reaction of a PAPA with an aldehyde wherein the PAPA has no hindered amine group.

It is therefore a general object of this invention to provide a process for selectively reductively alkylating a PAPA having a hindered primary amine group, comprising contacting said PAPA with hydrogen and a ketone in the presence of a catalytically effective amount of a Group VIII metal on a catalyst support, at a pressure in the range from about 500–1000 psi and a temperature in the range from about 50° C. to about 200° C. for a period of time sufficient to preferentially alkylate the unhindered primary terminal amine group, essentially without alkylating either the sterically hindered terminal primary amine group or the intermediate secondary amine group.

It is therefore a specific object of this invention to provide selectively reductively alkylated PAPA which may then be cyclized by the known "ketoform synthesis". Such cyclization is preferably effected using a readily available monoketone such as a lower aliphatic ketone having from 3 to about 20 carbon atoms, or a cycloaliphatic ketone, and chloroform which provides the carbonyl group in the polysubstituted piperazinone ("PSP") formed. By selecting the substituents in the PAPA, the molecular weight of the PSP may be tailored. One or more such PSPs are found to be essential reactants for the preparation of tailored stabilizers and stabilized compositions of this invention.

It has further been discovered that when a PSP is distally linked, through at least a three-atom chain of serially linked 1 (one) N and 2 (two) C atoms, to a triazine ring, the novel compounds so formed are found to be exceptionally well-suited for use as stabilizers in synthetic resinous materials subject to degradation by uv light.

It is therefore a general object of this invention to provide a novel class of hindered amine-triazine derivatives useful as ultraviolet (uv) light stabilizers for polyolefins and other light-degradable polymers, which derivatives are characterized by (a) having at least one substituted piperazinone slightly linked to a triazine ring, and (b) improved resistance to extraction from such polymers in prolonged contact with an aqueous solution.

It is also a general object of this invention to provide a simple and elegant process for making a distally linked 2-oxo-piperazinyl-triazine ("PIP-T" for brevity) from a particular class of alkylated PAPA, namely a N-(alkyl)-

N'-(aminoalkyl/aryl/aralkyl/cycloalkyl)-1,p-alkanediamine, wherein "p" is the number of methylene C atoms (hereafter "2AAD" for brevity), and a triazine compound reactive therewith. The process comprises reductively alkylating a particular class of PAPA, such as a N'-(aminoalkyl/aryl/aralkyl/cycloalkyl)-1,p-alkanediamine (hereafter "2AD" for brevity) with a ketone in the presence of a Group VIII metal hydrogenation catalyst and a solvent for the reactants, by carrying out the reaction under elevated temperature and pressure to produce the 2AAD compound; separating the solvent from the reaction mass; adding chloroform and a ketone, preferably in the presence of a phase transfer catalyst; and, carrying out the reaction to produce a PSP which is recovered. The PSP is then reacted with cyanuric chloride or other reactive triazine compound. In a particular preferred embodiment of the invention, a PSP is produced from 2AD using a ketone as a reactant to produce 2AAD; and then, aging using a ketone as a reactant, to cyclize the 2AAD. The PSP is then coupled with a triazine ring-containing compound to provide at least one distally linked PSP substituent on the triazine ring.

It is another general object of this invention to provide a combination stabilizer for PS and AO stabilization of polymers, particularly polyolefins, in which combination an effective amount of each of two compounds is used, one from the class of PS compounds containing linked triazine and piperazinone rings, and the other a hindered phenol selected from the group consisting of tris(3,5-di-t-butyl-4-hydroxybenzyl-)isocyanurate; 2,6-diteriarybutyl-p-cresol commercially available as "BHT", and 2,2'-ethylidenebis(4,6-ditertiarybutylphenol) commercially available under the brand Isonox 129; and, octadecyl-3,5-di-t-butyl-4-hydroxybenzenepropionate.

It is a specific object of this invention to provide a stabilized polymeric composition comprising a polymer of a mono-1-olefin having incorporated therein a small but effective, stabilizing amount, sufficient to stabilize the composition against the deleterious action of oxygen, heat and ultraviolet light, of (a) at least one polysubstituted piperazinone linked to a triazine nucleus, and (b) at least one hindered phenol selected from the group consisting of tris(3,5-di-t-butyl-4-hydroxybenzyl-)isocyanurate; 2,6-ditertiarybutyl-p-cresol; 2,2'-ethylidenebis(4,6-ditertiarybutylphenol); and, octadecyl-3,5-di-t-butyl-4-hydroxybenzenepropionate commercially available as Irganox 1076.

It is another specific object of this invention to provide an unexpectedly effective combination of (a) an oligomer having from 2 to 10 repeating units, each one of which includes a triazine ring distally connected to at least one piperazinone ring which has four lower alkyl substituents on the piperazinone ring, two on each side of the $N^4$ atom, and, (b) a particular hindered phenol selected from the group consisting of Goodrite ®3114; BHT and Isonox ®129; each component (a) and (b) being present in an amount in the range from 0.1 to about 1 phr; which combination, when essentially homogeneously dispersed in a polyethylene or polypropylene film or fiber enhances both its (the film or fiber's) resistance to degradation by light, and also to heat and oxygen.

DETAILED DESCRIPTION OF PREFERRED EMBODIMENTS

The basic structure of the stabilizer compounds prepared by the synthesis described herein, is a substituted triazine ring, to at least one carbon atom of which, is attached a substituted piperazinone by means of a linking group containing a nitrogen atom and at least two carbon atoms. The substituted piperazinone is preferably substituted at both the 3 and 5 positions with alkyl substituents, and the piperazinone substituent is therefore referred to as being 'polysubstituted'. A polysubstituted piperazinone is linked to a triazine ring as described, to produce a 2-oxo-piperazinyl-triazine ("PIP-T") which is the stabilizer of this invention, and which may be represented by the following formula (I):

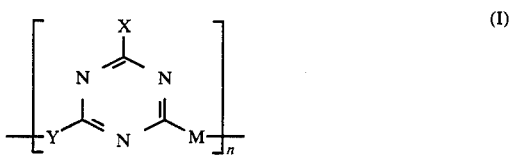

wherein,
n is an integer in the range from 1 to about 10, said compound having functional end groups selected from H, OH and Cl when n is greater than 1;
X is a substituent having the following formula (II):

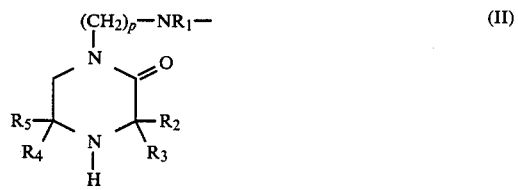

wherein,
$R_1$ represents alkyl having from 1 to about 24 carbon atoms, cycloalkyl having from 5 to about 7 carbon atoms, aralkyl having from 7 to about 20 carbon atoms, azaalkyl having from 1 to about 24 carbon atoms, and azacycloalkyl having from 6 to about 20 carbon atoms;
$R_2$, $R_3$, $R_4$ and $R_5$ independently represent alkyl having from 1 to about 24 carbon atoms;
p represents an integer in the range from 2 to about 10;
Y may be the same as X or M;
M may be Z or Z', wherein
Z represents a radical selected from the group consisting of Cl,

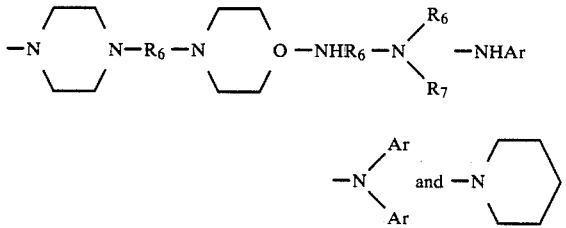

$R_6$, $R_7$ represent alkyl having from 2 to about 24 carbon atoms;

Ar represents aryl;

Z' represents a radical selected from the group consisting of

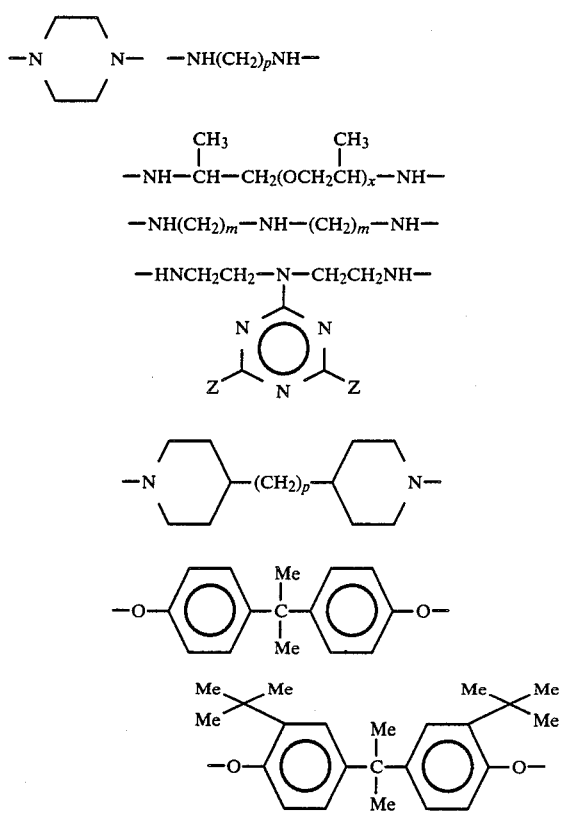

Me=methyl x represents an integer in the range from 1 to about 50;

m represents an integer in the range from 2 to about 4; and, when n=1, Y and M may be the same as X.

Particular monomeric PIP-T compounds of this invention may be represented by the following formula (III):

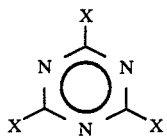

(III)

wherein, X has the same connotation as hereinabove.

Other monomeric PIP-T compounds of this invention may be represented by the following formula (IV):

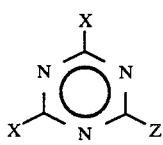

(IV)

wherein, X and Z have the same connotation as hereinabove.

Particular PIP-T bis-compounds of this invention may be represented by the following formula (V):

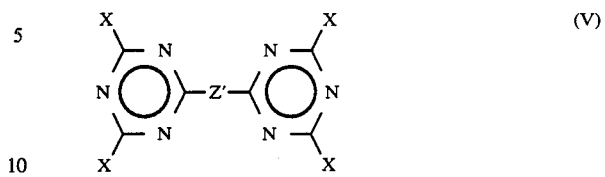

(V)

wherein, X and Z' have the same connotation as hereinabove.

Still other PIP-T compounds are oligomers of the substituted triazine ring, and may be represented by the following formula (VI):

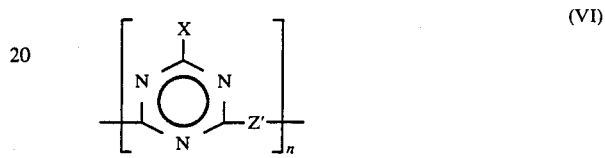

(VI)

wherein,
an oligomer is terminated with functional end groups selected from H, OH and Cl, and X, Z' and n have the same connotation as hereinabove.

In monomeric PIP-T compounds, Z and Z' each includes a terminal functional group selected from H, lower alkyl having from 1 to about 5 carbon atoms, and hydroxylalkyl having from 1 to about 5 carbon atoms.

It is especially significant that these relatively high molecular weight compounds contain a substituted piperazinone moiety distally linked to a substituted triazine moiety, in each of which moieties, namely the substituted piperazinone, the substituted triazine, and the link therebetween, groups may be independently substituted with other groups to produce stabilizers having not only desirable uv light stabilizing properties, but also heat stabilizing properties complemented with suitable solubility and dispersability. The substituted piperazinones together with the linking substituent are also referred to herein as polysubstituted piperazinones ("PSP" for brevity).

The substituted PIP-T compounds are generally oils or high melting crystalline solids soluble in acetone, diethyl ether, dioxane, tetrahydrofuran, carbon tetrachloride, chloroform, lower primary alcohols having from 1 to about 5 carbon atoms such as methanol, ethanol and propanol, aromatic hydrocarbons such as benzene and toluene, but much less soluble in aliphatic hydrocarbons such as hexane. Substituted PIP-T compounds are generally insoluble in water; they range in color from white to dark brown when pure.

The amount of stabilizer employed will vary with the particular material to be stabilized and also the substituted PIP-T employed. Generally however, for effective uv light stabilization of organic materials, an amount of the PIP-T used is in the range from about 0.001 percent to about 10 percent by weight (% by weight) based on the weight of organic material. In typical stabilized compositions the amount of substituted PIP-T used is in the range from about 0.01 to about 5% by weight.

Compositions of this invention are synthetic resinous materials which have been stabilized to combat the deleterious effects of uv light, thermal or oxidative degradation such as are usually evidenced by discoloration and/or embrittlement. These compositions generally benefit from the inclusion of additional, secondary stabilizers to achieve even greater stability against a combination of actinic light, heat and oxygen. Therefore, in conjunction with the stabilizers of this invention, compositions may include stabilizers against degradation by heat and/or oxygen which secondary stabilizers may be present in the range from about 0.1 part to about 10 parts by weight, and preferably from about 0.2 part to about 5 parts by weight per 100 parts by weight of the organic continous phase. Several types of known UV secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethylacrylates, poly-carbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The substituted PIP-T compounds can also be used to stabilize mixtures and blends of polymeric materials such as ABS resin blends, PVC and polymethacrylate blends, and blends of polyolefin homopolymers and copolymers such as blends of polypropylene in epdm polymers.

Most particularly substituted PIP-T compounds of this invention having at least one 3,3,5,5-tetraalkyl piperazinone distally linked to a triazine ring, most preferably with additional substituents at one or both of the remaining substitutable positions on the triazine ring, are especially useful as uv-light-stabilizers for synthetic resinous materials which are at least partially permeable to visible light, and particularly for those which are transparent thereto, such as the polyvinylaromatics and polyolefins.

Many known compounding ingredients may be used along with the substituted PIP-T stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like.

Particularly desirable secondary stabilizers are one or more antioxidants used in the range from about 0.1 part to about 20 parts by weight, preferably from about 0.2 part to about 5 parts by weight per 100 parts by weight of the material. Of the types of antioxidants to be used, are phosphite, phosphate, sulfide and phenolic antioxidants, the last being preferred. Most preferred are phenolic antioxidants such as 2,6-di-t-butyl paracresol; 2,2'-methylene-bis(6-t-butyl-phenol); 2,2'-thiobis(4-methyl-6-t-butyl-phenol); 2,2'-methylene-bis(6-t-butyl-4-ethylphenol); 4,4'-butylidene-bis(6-t-butyl-m-cresol); 2-(4-hydroxy-3,5-di-t-butylanilino)-4,6-bis(octylthio)-1,3,5-triazine; 1,3,5-tris-(3,5-di-t-butyl-4-hydroxyphenyl)-propionyl-s-triazine; hexahydro-1,3,5-tris-(3,5-di-t-butyl-4-hydroxybenzyl)isocyanurate; tetrakis-[methylene-3-(3',5'-di-t-butyl-4'-hydroxyphenyl)propionate]methane; and other antioxidant synergists such as distearyl thiodipropionate; dilauryl thiodipropionate; tri(nonylphenyl)-phosphite; tin thioglycolate; and particularly commercially available antioxidants such as Goodrite®3114, and 3125, Irganox 1010, 1035, 1076 and 1093. Other ingredients such as pigments, tackifiers, flame retardants, fungicides, and the like may also be added.

The substituted PIP-T stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a compositon which may be extruded, pressed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a substituted PIP-T to an organic material is either to dissolve or suspend the compound in a liquid such as hexane or benzene before adding it, or to add the PIP-T directly to the polymeric organic material whether the PIP-T is in the form of a powder or oil, or to extruder-mix the PIP-T and the polymeric material prior to forming the product. The uv stability of a particular composition containing a polymeric material and a substituted PIP-T can be evalutated by exposing a prepared sample of the composition to Xenon or carbon arc light in a Weather-O-meter operating at a temperature, for example, about 140° F. (60° C.). Degradation of the sample can be followed by periodically measuring tensile strength left, and the hydroperoxide absorption band at 3460 cm$^{-1}$ or carbonyl absorption band at 1720 cm$^{-1}$ using an IR spectrophotometer. The rapid formation of carbonyl indicates failure of the sample. The test procedure is well known, and is published in the text *Photodegradation, Photo-oxidation and Photostabilization of Polymers* by Ranby and Rabek, John Wiley & Sons, N.Y., N.Y. (1975), at pages 129 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C., and other standard ASTM tests such as tensile strength tests.

The method for making the PIP-T compounds of this invention starts with the preparation of a 2AAD compound or other alkylated PAPA, by reductive alkylation of a 2AD or other PAPA compound in the presence of a ketone reactant. Though reductive alkylation is a well known reaction, particularly for the preparation of amines, as taught for example in Chapter 3 entitled "The Preparation of Amines by Reductive Alkylation" by Emerson, William S., referred to hereinbefore, no PAPA with one hindered primary amine was alkylated. It is surprising that the reductive alkylation reaction carried out on a PAPA with a ketone and a Group VIII metal catalyst, or other known metal reductive alkylation catalyst, selectively provides alkylation at the 1-N atom of the amine being alkylated, without alkylating any other amine group.

The 2AD compound, such as for example, N-(2-amino-2-methylpropyl)-1,2-ethanediamine, is conveniently prepared from readily available raw materials by any method well known in the art.

In a second step, the 2AAD compound is used as a reactant in a ketoform reaction in the presence of an excess of a carbonyl-containing compound, preferably accelerated with a onium catalyst, to yield a PSP. In the third step, the PSP obtained is coupled with a triazine compound reactive therewith, most preferably cyanuric chloride, or an oligomer of a substituted triazine having a reactive functional end group through which the triazine compound is coupled with the PSP, so as to produce the PIP-T compound.

PREPARATION OF 2AAD COMPOUND

In a typical reaction, the 2AAD compound is prepared from N-(2-amino-2-methylpropyl)-1,2-ethanediamine and a ketone selected to provide the desired steric hindrance in the 2AAD compound, as illustrated in the following example 1.

EXAMPLE 1

Preparation of N-(2-butyl)-N'-(2-amino-2-methylpropyl)-1,2-ethanediamine having the following structure

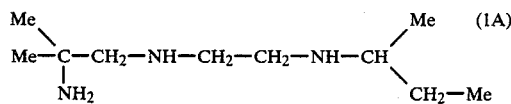

A mixture of 146 g (1.1 moles) of N-(2-amino-2-methylpropyl)-1,2-ethanediamine, 84.4 (1.17 moles) of 2-butanone, 300 ml methanol, and 3.0 g of 10% platinum on carbon were reacted in a 1 liter autoclave at 80° C. under 800 pounds per square inch (psi) hydrogen pressure. After two hours the reaction mixture was cooled, then filtered to remove the catalyst. The filtrate was stripped to give 205.3 g of water-white clear liquid which was fractionally distilled under reduced pressure. The desired product recovered was found to weigh 144.5 g (69.5% yield), and has a boiling point (b.p.) of 62°–64° C./0.15 mm Hg.

The structure written hereinabove is supported by both proton nuclear magnetic resonance (nmr), and field desorption (FD) mass spectroscopic data.

In an analogous manner, other dialkyl substitients may be substituted at the N position. For example, N-(4-methyl-2-pentyl)-N'-(2-amino-2-methylpropyl)-1,2-ethanediamine may be prepared from N-(2-amino-2-methylpropyl)-1,2-ethanediamine and 4-methyl-2-pentanone by reductive alkylation in propanol. The compound is obtained in excellent yield and is found to have a b.p. of 100°–109° C./0.3 mm Hg.

Alkylated PAPA in general, and the 2AAD compounds in particular, are useful for the curing of epoxy resins, and also as fungicides.

The foregoing selective reductive alkylation process may be effectively practiced with any PAPA having the general structure:

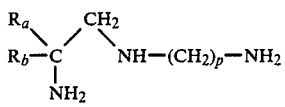

wherein, $R_a$ and $R_b$ independently represent alkyl having from 1 to 24 carbon atoms, aralkyl having from 7 to about 20 carbon atoms;

$R_a$ or $R_b$ may be cycloalkyl; or, $R_a$ and $R_b$ together when cyclized may be cycloalkyl having from 5 to about 7 carbon atoms; and, p has the same connotation as hereinabove.

When the process is practiced with a lower aliphatic ketone having from about 3 to about 20 carbon atoms, or a cycloaliphatic ketone having from 5 to about 20 carbon atoms and hydrogenation is effected over a Group VIII metal on a suitable catalyst support at a pressure in the range from about 500 psi to about 1000 psi and a temperature in the range from about 50° C. to about 200° C., no reaction product is isolated which is alkylated at either the intermediate amine group or the hindered terminal amine group.

Preparation of N-(2-propyl)-N'-(2-amino-2-methylpropyl)-1,2-ethanediamine also identified alternatively as N¹-(2-N-isopropylaminoethyl)-2-methyl-1,2-propanediamine, having the following structure

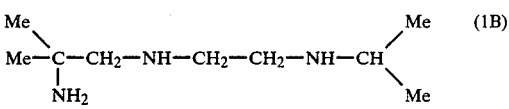

In a stirred autoclave place a mixture of 146 g of N-(2-amino-2-methylpropyl)-1,2-ethanediamine, 64 g acetone, 250 ml of methanol, and 20 g Raney's nickel, and hydrogenate the mixture under 1500 psi $H_2$ pressure in the autoclave heated and maintained at 150° C. After about 5 hr the reaction mixture is cooled, filtered to remove the catalyst, and concentrated. The desired product is obtained in 80% pure form which may be distilled at 90°–95° C./8 mm to yield a colorless oil. The pure product boils at 96°–98° C./8 mm of Hg.

The structure written above is supported by both proton nuclear magnetic resonance (nmr), and field desorption (FD) mass spectroscopic data.

Also in an analogous manner, a cycloalkyl, an aryl or aralkyl substituent may be substituted at the N position as for example, by preparing N-cyclohexyl-N'-(2-amino-2-methylpropyl)-1,2-ethanediamine having the following structure:

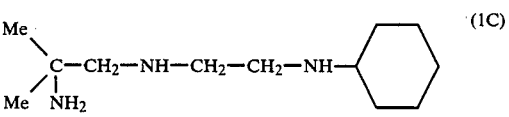

The desired compound is obtained by reacting N-(2-amino-2-methylpropyl)-1,2-ethanediamine with cyclohexanone in methanol in the presence of 10% Pt on carbon by hydrogenation at 80° C. under 800 psi. The desired compound is obtained by fractionation at reduced pressure and has a b p of 96°–104° C. at 0.7 mm Hg.

PREPARATION OF POLYSUBSTITUTED PIPERAZINONE ("PSP")

In a typical reaction, the PSP is prepared by the ketoform synthesis more fully described in U.S. Pat. No. 4,167,512, the disclosure of which is incorporated by reference thereto as it fully set forth herein. This synthesis is generally carried out with 1,2-diamines which are reacted with a saturated or unsaturated monoketone and certain aromatic aldehydes such as benzaldehyde, along with a haloform reactant, in an organic solvent for the reactants, in the presence of aqueous or solid alkali and a phase transfer catalyst. Though the phase transfer catalyst accelerates the reaction, it is now found to proceed quite well even in the absence of the phase transfer catalyst, provided the carbonyl reactant is a ketone and it is present in large excess. By large excess we refer to an amount in the range from 2 to 20 times the theoretical amount required. The reaction with a ketone proceeds at room temperature or below, though it may also be carried out at elevated temperatures, depending upon the particular other reactants present. A preferred temperature range is from about $-10°$ C. to about 30° C.

The ketoform synthesis as now practiced in the present invention is likewise carried out preferably in the same relatively low temperature range, preferably in the presence of a phase transfer catalyst and an alkali metal hydroxide, and chloroform. However, it differs from the prior art synthesis in that only a ketone will provide a recoverable amount of cyclized PSP. Preferred ketones are aliphatic monoketones having from 3 to about 12 carbon atoms, and cyclic monoketones having from about 6 to about 8 carbon atoms. Most preferred are the lower aliphatic ketones such as acetone including those having up to about 12 carbon atoms, and the cycloaliphatic ketones such as cyclohexanone which may be substituted. By 'recoverable amount' I refer to more than a trace amount, and particularly to an amount which can be recovered in typical laboratory equipment without undue difficulty.

A particular PSP is conveniently synthesized from a 2AAD compound as illustrated in the following example 2.

EXAMPLE 2

Preparation of 1-[2-(2-butylamino)ethyl]-3,3,5,5-tetramethyl-2-piperazinone having the following structure

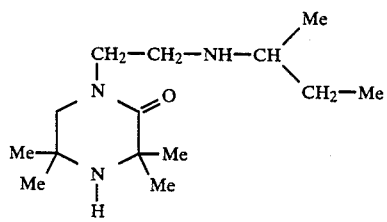

(2A)

In a 1 liter three-necked flask were placed 131.1 g (0.7 mole) of N-(2-butyl)-N'-(2-amino-2-methylpropyl)-1,2-ethanediamine, 101.6 g (1.75 moles) of acetone, 100.2 g (0.84 mole) of chloroform, 200 ml dichloromethane, and 7.9 g of 18-Crown-6 polyether phase tranfer catalyst. To this cooled mixture was added 224 g of 50% aqueous sodium hydroxide solution dropwise over a period of about 5 hours. After allowing the reaction to proceed overnight at about $-4°$ C. the reaction temperature was gradually raised to 5° C. and maintained at this temperature for an additional 5 hours. After the usual work-up, the organic layer was stripped and distilled (b.p. 115°–120° C./0.25 mm Hg) to collect 71.5 g of very light straw colored syrup which was at lest 98% pure as shown by gas chromatography.

The structure written hereinabove was confirmed by proton nmr and FD spectroscopic data.

In an analogous manner, by reaction with N-(1,3-dimethylbutyl)-N'-(2-amino-2-methylpropyl)-1,2-ethanediamine, acetone and chloroform, preferably in the presence of an effective amount of a phase transfer catalyst sufficient to produce the desired PSP compound, a compound having the following structure is obtained:

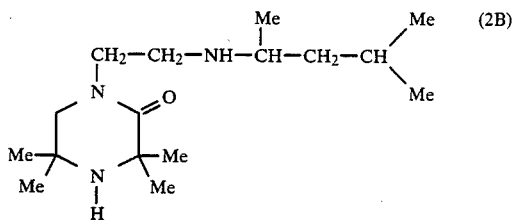

(2B)

The reaction occurs overnight at 3° C. and the reaction mass is worked up to produce about a 50% yield of the product which has a b p of 131°–3° C./0.5 mm Hg.

Also in an analogous manner, by reaction with N-(2-amino-2-methylpropyl)-N'-(cyclohexyl)-1,2-ethanediamine, acetone and chloroform in methylene chloride, a PSP compound having the following structure is obtained:

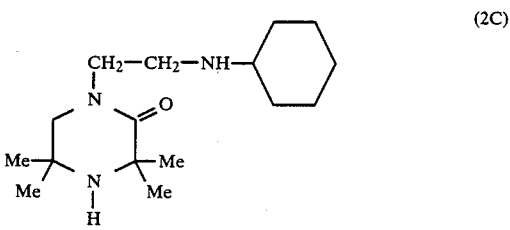

(2C)

As before, the reaction is allowed to proceed overnight, after which the desired product recovered is found to have a b p of 145°–6° C./0.7 mm Hg, with a yield of about 50% of theoretical.

PREPARATION OF PIP-T

The PSP obtained as described hereinabove is then coupled by reaction with a reactive triazine compound to yield a PIP-T. The triazine compound may be a monomeric triazine ring with functional groups reactive with the PSP, or the triazine compound may be an oligomer of a substituted triazine in which the repeating unit has functional groups which, in the oligomer are terminated with H, OH, or Cl atoms. The reaction is preferably carried out at ice-bath temperatures and ambient pressure, though in many instances a temperature of about 20° C. is convenient and even higher temperatures in the range from about room temperature to about 60° C. are practical. Typically, a PIP-T may be prepared as illustrated in the following example 3.

EXAMPLE 3

Preparation of 2,4-dichloro-6-[1-methylpropyl[2-(3,3,5,5-tetramethyl-2-oxo-1-piperazinyl)ethyl]amino]-1,3,5-triazine having the following structure

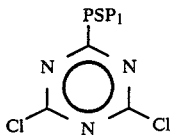
(3A)

wherein, PSP$_1$ represents

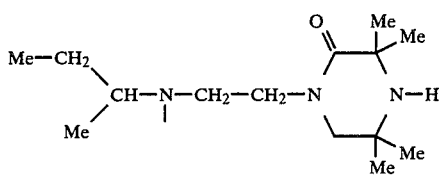

In a 1 liter three-necked flask were placed 300 ml of water which was cooled to 1° C. 46.1 g (0.25 mole) of cyanuric chloride was dissolved in 240 ml acetone and added to the water in the flask. A white slurry formed which was stirred while adding to it dropwise, 63.9 g (0.25 mole) of 1-[2-(2-butylamino)ethyl]-3,3,5,5-tetramethyl-2-piperazinone in 60 ml acetone and 13.3 g of sodium carbonate in 60 ml water. The addition took about 30 min.

The reaction was allowed to proceed for about 5.5 hours at about −7° to 9° C., after which the slurry was filtered to isolate a white solid. After washing with 750 ml of water and drying the product obtained wieghed 77.7 g and had a melting point (mp) of 91°-6° C. A pure sample was prepared for analysis by recrystallizing the product from hexane-toluene (2:1 ratio) and the solid obtained had a m pt of 93°-5° C.

Theoretical calculation for a compound $C_{17}H_{28}Cl_2N_6O$ gives the following: C=50.62; H=7.00; Cl=17.58; N=20.84. The analyzed product was found to have: C=49.84; H=6.89; Cl=17.94; N=20.70.

In an analogous manner other PSPs may be distally linked to the triazine ring. If the reaction is allowed to proceed further, and slightly in excess of 2 moles of a PSP are provided for each mole of the triazine compound, a second PSP is distally linked to each triazine ring which in turn is already substituted with a PSP. The PIP-T so formed has the following structure:

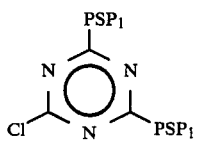
(3B)

If the reaction is allowed to proceed still further, and in excess of about 3 moles of a PSP are made available for each mole of triazine ring compound in the coupling reaction, a third PSP substituent may be distally linked to each triazine ring which already has two distally linked PSP substitutents. The PIP-T so formed has the following structure:

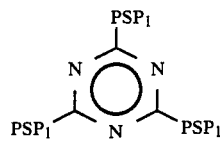
(3C)

In a manner analogous to that described in Example 3 hereinabove, by reacting [2-(1,3-dimethylbutylamino)ethyl]-3,3,5,5-tetramethyl-2-piperazinone dissolved in acetone, and sodium carbonate dissolved in water, added through separate funnels to a fine slurry of cyanuric chloride in acetone, a PIP-T compound having the following structure is obtained:

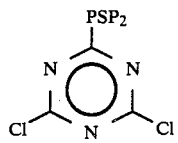
(3D)

wherein, PSP$_2$ represents

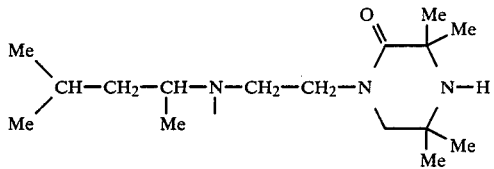

The compound, identified as 2,4-dichloro-6-[1,3-dimethylbutyl[2-(3,3,5,5-tetramethyl-2-oxo-1-piperazinyl)ethyl]amino]-1,3,5-triazine is obtained in about 56% yield, and has a bp of 57°-61° C.

If about 2 moles of the PSP$_2$ are added, and the reaction allowed to proceed until all the PSP$_2$ is reacted, then a second PSP$_2$ is distally linked to each triazine ring; and, if more than about 3 moles of PSP$_2$ are added and the reaction allowed to proceed, a third PSP is distally linked to the triazine ring, in a manner analogous with that described hereinabove.

EXAMPLE 4

Preparation of 2,4-bis(1-piperidinyl)-6-[1-methylpropyl[2-(3,3,5,5-tetramethyl-2-oxo-1-piperazinyl)ethyl]amino]-1,3,5-triazine having the structural formula

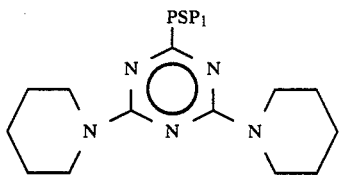
(4A)

A mixture of 4.03 g (0.01 mole) of 2,4-dichloro-6-[1-methylpropyl-[2-(3,3,5,5-tetramethyl-2-oxo-1-piperazinyl)ethyl]amino]-1,3,5-triazine with 1.87 g (0.022 mole) piperidine and 0.88 g sodium hydroxide in 150 ml toluene were reacted at 150° C. for 12 hours in a 300 ml autoclave. The reaction mass was cooled and filtered to remove sodium chloride. Concentration of the filtrate left an oil which solidified upon cooling. This off-white solid was the crude product weighing 5.03 g. An analytical sample was prepared by recrystallization of the crude solid from hexane. The recrystallized product had a mp of 126°–128° C. The structure given above was confirmed by nmr and FD mass specetroscope analysis.

In an analogous manner, 2,4-bis(1-piperidinyl)-6-[1,3-dimethylbutyl-[2-(3,3,5,5-tetramethyl-2-oxo-1-piperazinyl)ethyl]amino]-1.3,5-triazine having the following structure is prepared:

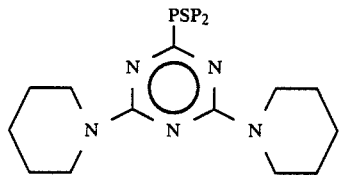
(4B)

by reacting 0.01 mole 2,4-dichloro-6-[1,3-dimethylbutyl[2-(3,3,5,5-tetramethyl-2-oxo-1-piperazinyl)ethyl]amino]-1,3,5-triazine with 0.022 mole piperidine. An analytical sample of the product obtaied had a mp of 141.5°–142.5° C. In a manner analogous to that described immediately hereinabove, a compound identified as 2,4-bis(1-piperidinyl)-6-[cyclohexyl[2-(3,3,5,5-tetramethyl-2-oxo-piperazinyl)ethyl]amino]-1,3,5-triazine having the following structure is obtained:

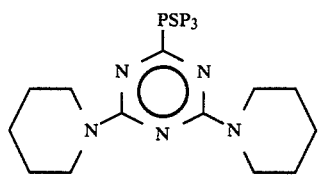
(4C)

wherein, PSP$_3$ represents

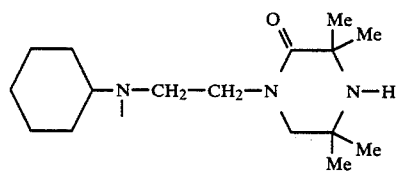

by reacting 2,4-dichloro-6-[cyclohexyl [2-(3,3,5,5-tetramethyl-2-oxo-1-piperazinyl)ethyl]amino]-1,3,5-triazine with piperidine, in the presence of sodium hydroxide and toluene, as before. The compound recovered has a mp of 179°–181° C.

The compound 2,4-bis(4-morpholinyl)-6-[cyclohexyl[2-(3,3,5,5-tetramethyl-2-oxo-1-piperazinyl)ethyl]amino]-1,3,5-triazine having the following structure:

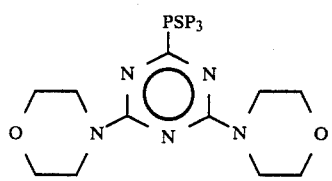
(4D)

is prepared by reacting 2,4-dichloro-6-[cyclohexyl[2-(3,3,5,5-tetramethyl-2-oxo-1-piperazinyl)ethyl]amino]-1,3,5-triazine and 0.022 mole morpholine. Recrystallization of the product from acetone gave a white solid. The structure of the solid was confirmed by nmr and FD mass spectrometer analysis.

In a manner analogous to that described hereinabove, a compound identified as 2,4,6-tris[cyclohexyl[2-(3,3,5,5-tetramethyl-2-oxo-1-piperazinyl)ethyl]amino]-1,3,5-triazine which has the following structure:

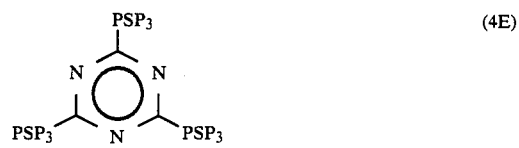
(4E)

is prepared by reacting 0.046 mole 1-[2-(cyclohexylamino)ethyl]-3,3,5,5-tetramethyl-2-piperazinone and 0.01 mole cyanuric chloride, 1.2 g sodium hydroxide and 150 ml toluene. The rection was carried out at 200° C. for 10 hr. The resulting light straw colored solid isolated was recrystallized from acetone and analyzed. It had a mp of 179°–180° C. and was off-white in color.

EXAMPLE 5

Preparation of 2,4-dichloro-6-[cyclohexyl[(1-cyclohexyl-3,3,5,-trimethyl-2-oxo-1-piperazinyl)methyl]amino]-1,3,5-triazine, a PIP-T having the structural formula:

(5A)

To 300 ml of water cooled to 1° C. in a three-necked flask are added 36.9 g (0.2 mole) of cyanuric chloride in 200 ml of hot acetone, forming a white slurry. To this slurry is added dropwise, 67.1 g (0.2 mole) of 1-cyclohexyl-5-cyclohexylaminomethyl-3,3,5-trimethyl-2-piperazinone in 50 ml of acetone and 10.6 g of sodium carbonate in 70 ml of water while the reaction temperature was maintained below 5° C. After reacting for 24 hr the resulting mixture was filtered to isolate 48.6 g of crude product which after recrystallization from toluene gave a white solid having a mp 123°–125° C.

EXAMPLE 6

Preparation of 2,4-dichloro-6-[2-propyl-[2-(3,3,5,5-tetramethyl-2-oxo-1-piperazinyl)ethyl]amino]-1,3,5-triazine, a PIP-T having the following structural formula:

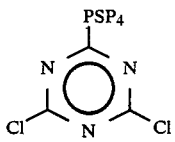

wherein, PSP$_4$ represents

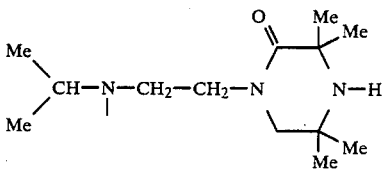

0.3 mole cyanuric chloride and 100 ml toluene were placed in a three-necked flask cooled in a melting ice bath, and 0.3 mole of 1-[2-(2-propylamino)ethyl]-3,3,5,5-tetramethyl-2-piperazinone in 70 ml toluene was added dropwise so as to maintain the temperature below 10° C. 20% NaOH solution (0.45 mole) was then added again keeping the temperature below 10° C. and the reaction mass was stirred overnight. The product collected was a solid (70 g) which had a mp 118°–121° C.

EXAMPLE 7

The Cl atoms in the PIP-T prepared in Example 6 hereinabove may each be replaced by reaction with an amine such as an aliphatic secondary amine, for example, a dialkylamine; or, a cyclic amine, for example, piperidine, morpholine and N-methylaaniline, the piperidine-substituted PIP-T giving the best results with respect to stabilization, both before and after extraction with water, as is evident from the data listed in Table I hereinbelow. The minimal difference in performance before and after extraction is evidence that the PIP-T compounds are not extracted with water.

The reaction of the PIP-T with an amine is carried out in toluene in the presence of 20% NaOH by heating in an autoclave at about 200° C. for 10 hr, after which the reaction mass is cooled and separated into two layers. The aqueous layer is dried and concentrated to yield a solid which is then recrystallized.

The PIP-T with both Cl atoms substituted has the following structural formula:

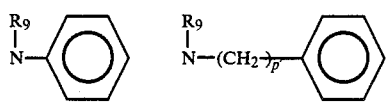

(7A)

where $NR_8$ represents the replacement amine, wherein $R_8$ is selected from the group consisting of alkyl having from 1 to about 24 carbon atoms, cycloalkyl having from 5 to about 7 carbon atoms, phenyl, and aralkyl having from 7 to about 20 carbons atoms so that $NR_8$ is represented by the structure

wherein $R_9$ is alkyl, and the number of alkyl carbon atoms and alkylene carbon atoms p' is in the range from 1 to 14. When $HNR_8$ is piperidine, the piperidine-substituted PIP-T has a mp 127°–132° C.; when $HNR_8$ is morpholine the morpholine-substituted PIP-T has a mp 135°–138° C.; when $HNR_8$ is N-methylaniline the aralkylamine substituted PIP-T has a mp 115°–132° C.; and in each of the foregoing $NR_8$ is selected from piperidyl, morpholinyl and N-methylanilinyl and H is absent.

The Cl atoms in the PIP-T prepared in Example 6 hereinabove may also be replaced, one or preferably both, by reaction with a PSP as described in Example 3 hereinabove.

Thus, if 1 mole of cyanuric chloride in toluene is reacted with 2 moles of 1-[2-(iso-propylamino) ethyl]-3,3,5,5-tetramethyl-2-piperazinone followed by the addition of 2 moles aqueous NaOH (10%) slowly, at a temperature below about 35° C., a solid reaction product is isolated which has a mp 126°–130° C., and the following structure:

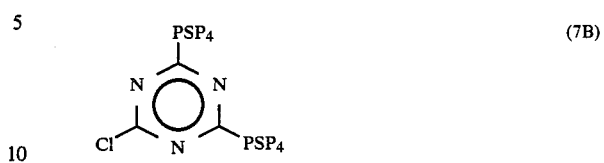

(7B)

If an additional (third) mole of 1-[2-(iso-propylamino)ethyl]-3,3,5,5-tetramethyl-2-piperazinone is reacted with each mole of cyanuric chloride, a PIP-T compound with the following structure results:

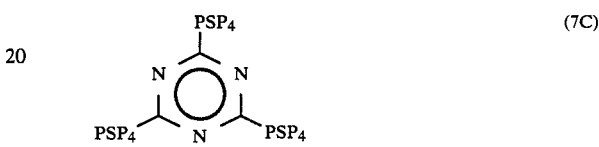

(7C)

The following Table I sets forth data obtained in tests conducted with 2 mil thickness samples of polypropylene. The blank and each sample includes 0.05 parts per hundred parts of resin ('phr') of Goodrite ® 3125 antioxidant, and the amount of stabilizer used in each sample is stated. Oven aging is done at 125° C. in the standard test procedure, and the Weather-O-Meter tests give the number of hours after which a sample loses 50% of its tensile strength. Chimasorb 944 is a commercially available polytriazine having piperidine substituents disclosed in U.S. Pat. No. 4,086,204.

TABLE I

| | | Xenon Weather-O-Meter (hr)** | |
|---|---|---|---|
| | Oven aging | Before | After |
| Stabilizer used | (days)* | H₂O extr. | H₂O extr. |
| Blank | 25 | 180 | 180 |
| Chimasorb 944 (0.1 phr) | 25 | 460 | 400 |
| Chimasorb 944 (0.05 phr) | 25 | 420 | 420 |
| PIP-T with PSP₄ substituent & both HNR₈ is piperidine | 22 | 1470 | >1600 |
| Compound (8A) (0.05 phr) | 33 | 460 | 370 |
| Compound (8A) (0.1 phr) | 53 | 600 | 430 |
| Compounds (8E') and (8E'') mixed in ratio 2:3 (0.05 phr) | 32 | 550 | 440 |

® Goodrite is a trademark of the B. F. Goodrich Company
**hours after which tensile strength left was 50% of strength before exposure
*days at 125° C. continuously

EXAMPLE 8

Other bis compounds in which two PIP-Ts are linked with a linking group by replacement of Cl atoms of the PIP-T may be prepared by reaction in a suitable solvent by the addition of aqueous NaOH, as taught in Example 4, inter alia, hereinabove.

A. Preparation of 1,1′,1″,1‴-[1,4-piperazinyl-1,3,5-triazine-6,2,4-triylbis[[iso-propylimino]-2,1-ethanediyl]]]tetrakis[3,3,5,5-tetramethylpiperazinone] having the following structure

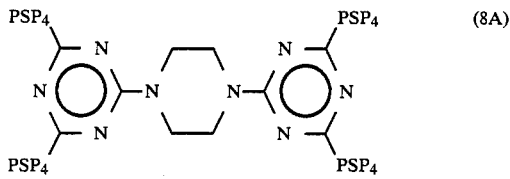

(8A)

0.01 mole of 2-chloro-4,6-bis[iso-propyl[2-(3,3,5,5-tetramethyl-2-oxo-1-piperazinyl)ethyl]amino]-1,3,5-triazine, 0.005 mole piperazine, 40 ml mesitylene and 0.12 mole 25% NaOH solution were refluxed under argon for about 12 hr. After cooling and filtration, 5 g of a white solid are collected.

B. Preparation of 1,1′,1″,1‴-[1,3-propanediylbis[4,1-piperidinyl-1,3,5-triazine-6,2,4-triylbis[[(cyclohexyl)imino]-2,1-ethanediyl]]]tetrakis[3,3,5,5-tetramethylpiperazinone] having the following structure:

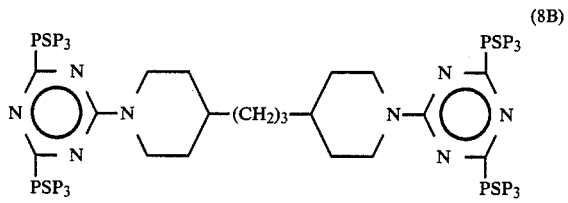

(8B)

4.72 g (7 m mole) of 2-chloro-4,6-bis[cyclohexyl[2-(3,3,5,5-tetramethyl-2-oxo-1-piperazinyl)ethyl]amino]-1,3,5-triazine, 0.74 g (3.5 m mole) of 4,4′-(1,3-propanediyl)bis(piperidine), 0.28 g of ground sodium hydroxide, and 150 ml of toluene were reacted at 150° C. for 10 hr, cooled and filtered. The white solid isolated had a mp 223°–233° C.

C. Preparation of 1,1′,1″,1‴-[1,4-piperazinyl-1,3,5-triazine-6,2,4-triylbis[[(cyclohexyl)imino]-2,1-ethanediyl]]]tetrakis[3,3,5,5-tetramethylpiperazinone] having the following structure

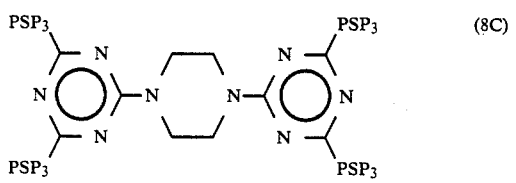

(8C)

4.72 g (7 millimole) of 2-chloro-4,6-bis[cyclohexyl[2-(3,3,5,5-tetramethyl-2-oxo-1-piperazinyl)ethyl]amino]-1,3,5-triazine, 0.30 g (3.5 m mole) of piperazine, 0.28 g ground sodium hydroxide, and 150 ml of toluene are reacted at 150° C. for about 15 hr after which, upon cooling and filtering, 2.6 g of an off-white solid are recovered. An analytical sample was prepared by recrystallization from ethyl acetate and methanol which sample had a mp 300°–309° C. The above structure was confirmed by FD mass spectrometry.

D. Preparation of 1,1′-[[6-[4-[2-[4,6-bis[cyclohexyl[2-(3,3,5,5-tetramethyl-2-oxo-1-piperazinyl)ethyl]amino]-1,3,5-triazine-2-yl]amino]ethyl]1-piperazinyl]-1,3,5-triazin-2,4-diyl]bis[cyclohexyl-imino-2,1-ethane-diyl]bis[3,3,5,5-tetramethylpiperazinone] having the following structure

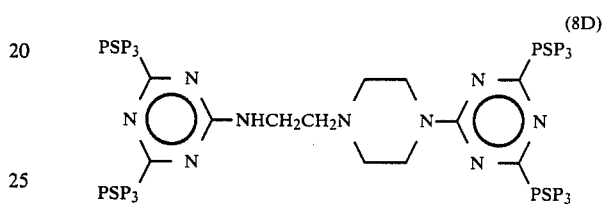

(8D)

6.07 g (9 m mole) of 2-chloro-4,6-bis[cyclohexyl[2-(3,3,5,5-tetramethyl-2-oxo-1-piperazinyl)ethyl]amino]-1,3,5-triazine, 0.58 g (4.5 millimole) of N-(2-aminomethyl)piperazine, 0.36 g ground sodium hydroxide, and 150 ml of toluene are reacted at 150° C. for about 16 hr after which, upon cooling and filtering, the filtrate was concentrated to a syrup to which 75 ml hexane was added. A light yellow solid was formed which upon recrystallization from hexane-acetone had a mp 115°–118° C.

It will be appreciated that in the preparation of the foregoing bis compounds, and other analogous bis compounds, the particular conditions of the reaction will influence the ratio of reaction products formed in the 'mix' which contains bis compounds other than (8A) and (8C) when each is prepared as described hereinbefore. For example, in the preparation of the bis compound (8A), in addition to this compound linked only with piperazine, a compound of the following structure is also formed:

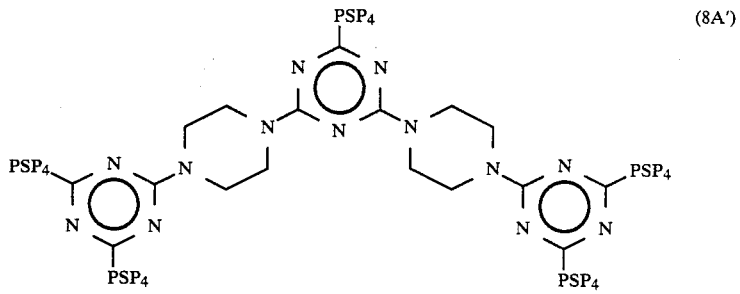

(8A′)

This PSP₄ compound (8A′) may be identified as 5,5′,5″,5‴-[[6-isopropyl[(1-isopropyl-3,3,5-trimethyl-2-oxo-5-piperazinyl)methyl]amino]-1,3,5-triazine-2,4-diyl]-bis[4,1-piperazinediyl-1,3,5-triazine-6,2,4-triylbis[[(isopropyl)imino]methyl]]]tetrakis[1-isopropyl-3,3,5-trimethylpiperazinone]. An analogous PSP₃ bis compound (8C') is also formed along with the compound (8C), and these bis compounds which are generally formed in a minor amount, from about 5 to about 40% of the mix, relative to the (8A) and (8C) compounds are also useful stabilizers.

E. Preparation of a mixture of 2-[(6-aminohexyl)amino]-4,6-bis[2,2,6,6-tetramethyl-4-piperidinyl[2-(3,3,5,5-tetramethyl-2-oxo-1-piperazinyl-)ethyl]amino]-1,3,5-triazine (identified as compound 8E'), and, 1,1',1'',1'''-[1,6-hexanediylbis[imino-1,3,5-triazine-6,2,4-triylbis[[(2,2,6,6-tetramethyl-4-piperidinyl)imino]-2,1-ethanediyl]]]tetrakis[3,3,5,5-teramethylpiperazinone] (identified as compound 8E'')

In a 100 ml three-necked flask were placed 2.37 g (3 mmole) of 2-chloro-4,6-bis[2,2,6,6-tetramethyl-4-piperidinyl[2-(3,3,5,5-tetramethyl-2-oxo-1-piperidinyl-)ethyl]amino]-1,3,5-triazine and 0.174 g (1.5 mmole) of 1,6-hexanediamine, 0.132 g NaOH and 65 ml dry xylene. After refluxing overnight, the reaction mixture was filtered to remove NaCl and the filtrate concentrated to a yellow oil to which hexane was added to form a pale yellow solid. Upon recrystallization from hexane 1.15 g of pale yellow solid, mp 65°–175° C. is obtained. A mass spectrographic (FD) analysis shows the product is a 2:3 mixture of compounds 8E' and 8E'' respectively. The reaction may be represented as follows:

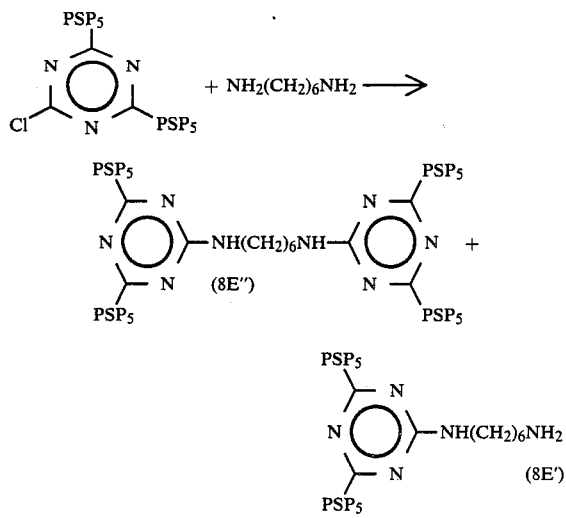

wherein PSP$_5$ represents

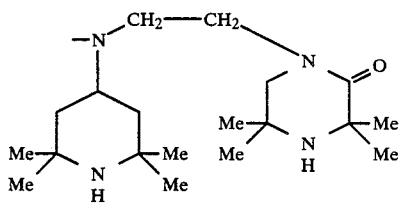

The test results for a mixture of (8E') and (8E'') is given in Table I.

PREPARATION OF PIP-T OLIGOMERS

In a typical reaction, the PIP-T oligomer is prepared from a dichloro-PIP-T compound and the appropriate compound desired as a substituent for the Cl atoms, in toluene or other suitable solvent usually in the presence of solid alkali metal, and the reaction is carried out under elevated pressure in an autoclave, as described in greater detail in the following examples.

EXAMPLE 9

A. Preparation of poly[[6-[1-methylpropyl[2-(3,3,5,5-tetramethyl-2-oxo-1-piperazinyl)ethyl]amino]-1,3,5-triazine-2,4-diyl]imino-1,6-hexanediylimino] having the following structure

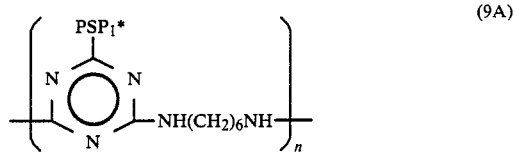

(9A)

*PSP$_1$ has the same connotation as before (see Example 3)

A mixture of 4.03 g (0.01 mole) of 2,4-dichloro-6-[1-methylpropyl[2-(3,3,5,5-tetramethyl-2-oxo-1-piperazinyl)ethyl]amino]-1,3,5-triazine, 1.22 g (0.0105 mole) of 1,6-hexanediamine, 0.84 g sodium hydroxide (ground solid), and 150 ml toluene were reacted at 155° C. for about 16 hours in a 300 ml autoclave under autogenously developed pressure in the autoclave. The reaction mixture is cooled, filtered and concentrated to isolate 2.4 g of light brown solid, from which 1.37 g of gray solid was collected after a water wash. This was combined with 1.69 g of yellow solid obtained from the filtrate (after stripping and water wash). The combined solids are ground and sieved through a No. 80 U.S. standard series sieve to yield a light gray powder which has a softening point of 160° C.

B. Preparation of poly[[6-[1-methylpropyl[2-(3,3,5,5-tetramethyl-2-oxo-1-piperazinyl)ethyl]amino]-1,3,5-triazine-2,4-diyl]oxy-1,4-phenylene(1-methylethylidene)-1,4-phenyleneoxy] having the following structure

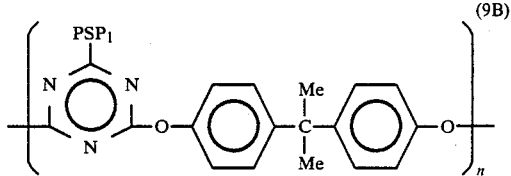

(9B)

In a manner analogous with that described hereinbefore in Example 9A, 0.01 mole of 2,4-dichloro-6-[1-methylpropyl[2-(3,3,5,5-tetramethyl-2-oxo-1-piperazinyl)ethyl]amino]-1,3,5-triazine, 0.0105 mole of 4,4'-(1-methylethylidene)bisphenol, in toluene and in the presence of finely ground NaOH are reacted at 155° C. for about 16 hr in 300 ml autoclave.

After the usual workup 4.2 g of light straw colored solid was isolated from the filtrate, which solid had a softening point of 88° C.

C. Preparation of
poly[[6-[1-methylpropyl[2-(3,3,5,5-tetramethyl-2-oxo-1-piperazinyl)ethyl]amino]-1,3,5-triazine-2,4-diyl]imino-1,4-cyclohexanediylmethylene-1,4-cyclohexanediylimino] having the following structure

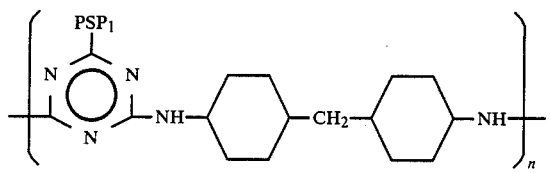

In a manner analogous with that described hereinbefore in Example 9A, 0.01 mole of 2,4-dichloro-6-[1-methylpropyl[2-(3,3,5,5-tetramethyl-2-oxo-1-piperazinyl)ethyl]amino]-1,3,5-triazine, 0.0105 mole of 4,4'-methylenebis(cyclohexylamine), in toluene and in the presence of finely ground NaOH are reacted at ] 50° C. for about 16 hr in a 300 ml autoclave.

After the usual workup, 3.2 g of pale yellow solid was isolated from the filtrate. When ground and sieved through a No. 80 mesh screen, an off-white solid is obtained which softens at 105° C.

D. Preparation of
poly[[6-[1-methylpropyl[2-(3,3,5,5-tetramethyl-2-oxo-1-piperazinyl)ethyl]amino]-1,3,5-triazine-2,4-diyl]imino-1,2-ethanediylimino] having the following structure

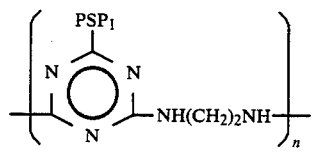

In a manner analogous with that described hereinbefore in Example 9A, but substituting 0.0105 mole of 1,2-ethanediamine for the 1,6-hexanediamine, the reaction carried out at 160° C. yields 3.41 g of light gray solid which softens at 80° C.

E. Preparation of
poly[[6-[1-methylpropyl[2-(3,3,5,5-tetramethyl-2-oxo-1-piperazinyl)ethyl]amino]-1,3,5-triazine-2,4-diyl]-1,4-piperazinediyl] having the following structure

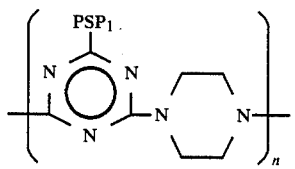

In a manner analogous with that described hereinbefore in Example 9A, but substituting 0.0105 mole of piperazine for the 1,6-hexanediamine, the reaction carried out at 150° C. for about 16 hr directly yields 0.87 g of a grayish solid upon filtration, and an additional 2.49 g of a pale yellow solid from the filtrate after it is stripped and washed with water. The solids are combined, ground and sieved as above to yield a very light gray powder which softens at 192° C.

F. Preparation of
poly[[6-[1-methylpropyl[2-(3,3,5,5-tetramethyl-2-oxo-1-piperazinyl)ethyl]amino]-1,3,5-triazine-2,4-diyl]imino-1,2-cyclohexanediylimino] having the following structure

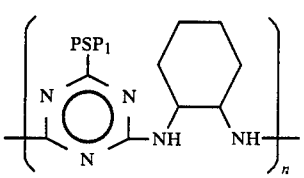

In a manner analogous with that described hereinbefore in Example 9A, but substituting 0.0105 mole of 1,2-cyclohexanediamine for the 1,6-hexanediamine, the reaction carried out at 150° C. for about 14 hr directly yields 3.5 g of yellow (brown tinted) solid which when ground and sieved softened at 105° C.

As will be evident from the foregoing examples, the oligomerization is best carried out at elevated temperature in the range from about 30° C. to about 300° C., and more preferably in the range from about 100° C. to about 250° C. Since the reactions are carried out in solvent, the pressure must be sufficient to avoid undue vaporization of solvent and will generally be above atmospheric, most preferably in the range from about 15 to about 100 psig, the higher pressures generally assisting the speed of the reaction.

EXAMPLE 10

In a manner analogous to that described hereinbefore in Example 9, PIP-T oligomers are prepared with other PSPs such as $PSP_2$, $PSP_3$, and $PSP_4$.

For example, with $PSP_2$ the following oligomers are prepared in a manner analogous with the $PSP_1$ oligomers:

10A. Corresponding to (9A) the compound (10A) may be identified as follows: poly[[6-[1,3-dimethylbutyl[2-(3,3,5,5-tetramethyl-2-oxo-1-piperazinyl)ethyl]amino]-1,3,5-triazine-2,4-diyl]imino-1,6-hexanediylimine]. The compound is recovered as a straw colored solid which, when ground to a powder, softens at 70° C.

10B. Corresponding to (9B) the compound (10B) may be identified as follows: poly[[6-[1,3-dimethylbutyl[2-(3,3,5,5-tetramethyl-2-oxo-1-piperazinyl)ethyl]amino]-1,3,5-triazine-2,4-diyl]oxy-1,4-phenylene(1-methylethylidene)-1,4-phenyleneoxy].

It is prepared in a manner analogous to the preparation of compound 10A, and specifically as follows: A mixture of 4.31 g (0.01 mole) of 2,4-dichloro-6-[1,3-dimethylbutyl[2-(3,3,5,5-tetramethyl-2-oxo-1-piperazinyl)-ethyl]amino]-1,3,5-triazine, 2.4 g (0.0105 mole) of 4,4'-(1-methylethylidene)bisphenol, 0.84 g sodium hydroxide (ground solid), and 150 ml toluene were reacted at 155° C. for about 16 hours in a 300 ml autoclave under autogenously developed pressure in the autoclave. The reaction mixture is cooled, filtered and concentrated to recover 5.16 g of a light strawcolored solid. When the solid is ground it is an off-white color and softens at 95° C.

10C. Corresponding to (9C) the compound (10C) may be identified as follows: poly[[6-[1,3-dimethylbutyl[2-(3,3,5,5-tetramethyl-2-oxo-1-piperazinyl)ethyl]amino]-1,3,5-triazine-2,4-diyl]imino-1,4- cyclohexanediylmethylene-1,4-cyclohexanediylimino]. The cyclohexanediylimino substituent linking the triazine nuclei in the oligomer is introduced by reacting 4,4'-methylenebis(cyclohexylamine) and recovering the reaction product with the usual workup, namely cooling, filtering and concentrating the reaction mixture. A light straw colored solid is recovered which, when ground, softens at 95° C.

10D. Corresponding to (9D), the compound (10D) may be identified as follows: poly[[6-[1,3-dimethylbutyl[2-(3,3,5,5-tetramethyl-2-oxo-1-piperazinyl)ethyl]amino]1,3,5-triazine-2,4-diyl]imino-1,2-ethanediamino]. The linking substituent is introduced by reacting 1,2-ethanediamine and recovering a light yellow solid after the usual workup. The solid softens at 125° C.

10E. Corresponding to (9E), the compound (10E) may be identified as follows: poly[[6-[1,3-dimethylbutyl[2-(3,3,5,5-tetramethyl-2-oxo-1-piperazinyl)ethyl]amino]-1,3,5-triazine-2,4-diyl]-1,4-piperazinediyl]. The linking substituent is introduced by adding piperazine. A pale yellow solid is recovered which when ground, softens at 170° C.

10F. Corresponding to (9F) the compound (10F) may be identified as follows: poly[[6-[1,3-dimethylbutyl[2-(3,3,5,5-tetramethyl-2-oxo-1-piperazinyl)ethyl]amino]-1,3,5-triazine-2,4-diyl]imino-1,2-cyclohexanediylimino]. The linking substituent is introduced by the addition of 1,2-cyclohexanediamine and the product recovered is a brown solid which, when ground, softens at 100° C.

In each of the foregoing examples 10A–10F, PSP$_2$ has the same connotation as hereinbefore (see Example 3D).

EXAMPLE 11

In a manner analogous to that described hereinbefore in Example 9 PIP-T oligomers are prepared with PSP$_3$ substituents, as illustrated below:

11A. Corresponding to (9A) the compound (11A) may be identified as follows: poly[[6-[cyclohexyl[(1-cyclohexyl-3,3,5-trimethyl-2-oxo-5-piperazinyl)methyl]amino]-1,3,5-triazine-2,4-diyl]imino-1,6-hexanediylimino] which is obtained as light yellow straw colored solid which was washed with water and dried. It has a softening point of 80° C.

11B. Corresponding to (9B) the compound (11B) may be identified as follows: poly[[6-[cyclohexyl[2-(3,3,5-tetramethyl-2-oxo-1-piperazinyl)ethyl]amino]-1,3,5-triazine-2,4-diyl]oxy-1,4-phenylene(1-methylethylidene)-1,4-phenyleneoxy] which is obtained as a straw colored solid softening at 100° C.

11C. Corresponding to (9C) the compound (11C) may be identified as follows: poly[[6-[cyclohexyl[2-(3,3,5,5-tetramethyl-2-oxo-1-piperazinyl)ethyl]amino]-1,3,5-triazine-2,4-diyl]imino-1,4-cyclohexanediylmethylene-1,4-cyclohexanediylimino] which is obtained as a light straw colored solid which softens a 115° C.

11E. Corresponding to (9E) the compound (11E) may be identified as follows: poly[[6-[cyclohexyl[(1-cyclohexyl-3,3,5-trimethyl-2-oxo-5-piperazinyl)methyl]amino]-1,3,5-triazine-2,4-diyl]-1,4-piperazinediyl] which is obtained as a light yellow solid softening at 115° C.

11F. Corresponding to (9F) the compound (11F) may be identified as follows: poly[[6-[cyclohexyl[(1-cyclohexyl-3,3,5-trimethyl-2-oxo-5-piperazinyl)methyl]amino]-1,3,5-triazine-2,4-diyl]imino-1,2-cyclohexanediylimino] which is obtained as a yellow (brown tint) solid which softens at 120° C.

In addition to the foregoing, the following PSP$_3$-substituted oligomers are prepared in a manner analogous to that described hereinabove:

EXAMPLE 12

12A. A compound identified as poly[[6-[cyclohexyl[2-(3,3,5,5-tetramethyl-2-oxo-piperazinyl)ethyl]amino]-1,3,5-triazine-2,4-diyl]oxy-1,4-[2-(1,1-dimethylethyl)]phenylene(1-methylethylidene)-1,4-[3-(1,1-dimethylethyl)]phenyleneoxy] having the following structure is obtained as a solid which softens at 90° C.:

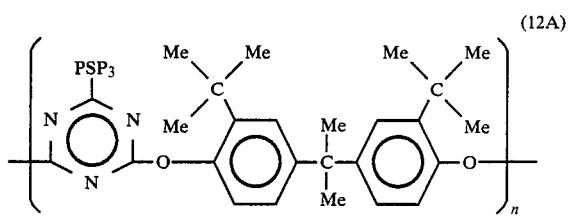

(12A)

12B. A compound identified as poly[[6-[cyclohexyl[2-(3,3,5,5-tetramethyl-2-oxo-1-piperazinyl)ethyl]amino]-1,3,5-triazine-2,4-diyl]imino-1,2-ethanediyl-1,4-piperazinediyl] having the following structure is obtained as a yellow to light brown solid which softens at 128° C.

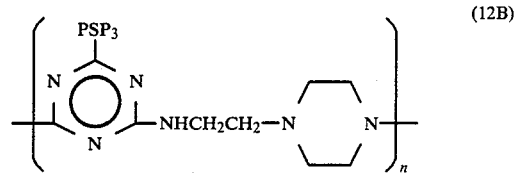

(12B)

12C. A compound identified as poly[[6-[cyclohexyl[2-(3,3,5,5-tetramethyl-2-oxo-1-piperazinyl)ethyl]amino]-1,3,5-triazine-2,4-diyl]imino-1,3-propanediyl-1,4-piperazinediyl-1,3-propanediylimino] is obtained as a light yellow solid having a softening point of 82° C., and has the following structure:

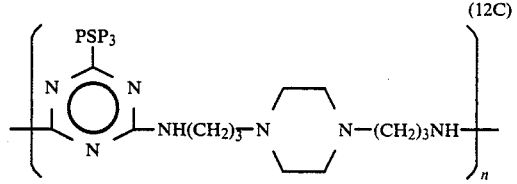

(12C)

12D. A compound identified as poly[[6-[cyclohexyl[1-cyclohexyl-3,3,5-trimethyl-2-oxo-5-piperazinyl)methyl]amino]-1,3,5-triazine-2,4-diyl]imino-1,2-ethanediyl-1,4-piperazinediyl] having the following structure is obtained as a yellow-brown solid which softens at 125° C.:

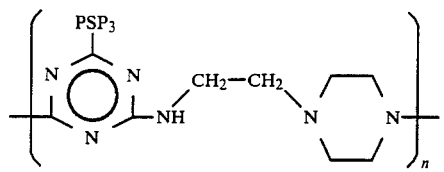

As will readily be ascertained, the molecular weights of the monomeric PIP-T compounds with a single triazine nucleus may be calculated from their structural formulae. For example the compound (3A) prepared in Example 3 will have a molecular weight of 96. The molecular weight of such a PIP-T may be increased by changing the substituents on the piperazinone, as well as those on the N atom linked to the triazine nucleus. Similarly, the molecular weight of a monomeric PIP-T with more than one triazine nucleus, such as the bis compounds illustrated in Example 8, may also be readily calculated.

The molecular weights of the oligomers will generally range from about 500 to about 5000, though higher molecular weights up to about 10,000 may be prepared with appropriate substituents. The molecular weights of oligomers are most preferably determined with a vapor pressure osmometer which provides a number average molecular weight ($\overline{M}n$). The molecular weight may also be obtained by mass spectrographic analysis, and if the molecular weight is above about 4000, gel permeation chromatography may be used.

EXAMPLE 13

Still other oligomers such as PSP$_4$-substituted oligomers illustratively listed herebelow in this example 13, were prepared in a manner analogous to that described hereinabove for the other oligomers. Thus, by reaction of N$^1$-(2-N-isopropylaminoethyl)-2-methyl-1,2-propanediamine with acetone and chloroform, both the latter in excess, and dripping in NaOH (the ketoform reaction), the PSP formed is 1-(2-N-isopropylaminoethyl)-3,3,5,5-tetramethyl-2-pieprazinone. This PSP is reacted with cyanuric chloride on a 1:3 molar basis so that the major portion of the substituted product, if not essentially all of it, is a PIP-T which is mono-substituted with the PSP$_4$. The 2,4-dichloro-6-N-(N-isopropyl-N-(2-(1,3,3,5,5-tetramethyl-2-piperazinone)ethylamino)-1,3,5-triazine (the PIP-T) is a solid (mp 118°–121° C.) which is reacted with an equimolar amount of a primary or secondary diamine chosen to provide a desired linking substituent in the oligomer, in the presence of aqueous alkali and toluene solvent, in an autoclave at about 200° C. for about 10 hr. When the reaction product is cooled, solids are filtered and the organic layer of the filtrate is concentrated to provide additional solid.

The reaction producing the oligomers may be written as follows:

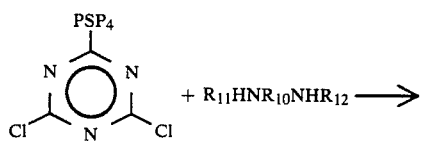

-continued

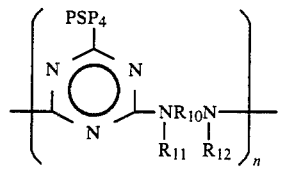

wherein,

R$_{10}$ represents alkyl having from 2 to about 24 carbon atoms, or cycloalkyl having from 5 to about 7 carbon atoms, and R$_{11}$ and R$_{12}$ independently represent H or alkyl having from 1 to about 24 carbon atoms with reactive functional groups.

The following diamines are conveniently used to provide a linking group for the oligomers which generally constitute from 3 to about 10 linked molecules depending upon the linking group.

| Diamine | Oligomer's melting point, °C. |
|---|---|
| piperazine | >250 |
| 1,6-hexanediamine | 125–145 |
| ethylenediamine | 205–285 |
| 1,3-propanediamine | 165–200 |
| methylamino-N,N—bis-(3-aminopropane) | 65–100 |
| p-phenylenediamine | >250 |

The number average molecular weights determined by vapor pressure osmometer for some of the oligomers prepared are listed hereinbelow:

| Oligomer | $\overline{M}n$ |
|---|---|
| 10C | 1350 |
| 10D | 1350 |
| 10E | 2430 |
| 10F | 1190 |
| 11A | 864 |
| 11B | 1440 |
| 11C | 790 |
| 11E | 1180 |
| 11F | 965 |

It will now be more readily appreciated that the preparation of the PIP-T compounds of this invention depends upon the ability to prepare the precursor piperazinone with the serially linked N and C atoms of the substituent bridge (to the triazine ring) at the N$^1$ position of the piperazinone. The preparation of the substituted piperazinone, in turn, depends upon the ability to preferentially selectively reductively alkylate a suitable PAPA. Having made the substituted piperazinone which itself has good uv-light stabilization properties, there was no reason to expect that connecting the piperazinone to a triazine nucleus, as illustrated in Example 6, would provide superior uv-stabilization compared with that provided by the substituted piperazinone alone. It does not. This result is consistent with the knowledge that trizaine by itself has no significant uv-stabilization properties. Yet, by introducing the additional substituted piperazinone substituents in the remaining two positions of the triazine ring, unexpectedly results in excellent uv-stabilization properties of the PIPT-T compounds. Alternatively, the remaining two positions on the triazine ring may be substituted with an amine as illustrated in Example 7A which also yields compounds with excellent u-v light stabilization properties.

It is most preferred, for practical reasons, to use a cyanuric halide, for example cyanuric chloride or bromide, as the reactant to form a PIP-T compound, though it will be appreciated that any triazine compound with a reactive functional group will serve the purpose. Compositions containing an effective amount of a PIP-T stabilizer in which two PSPs are linked to a triazine ring (as shown in the structural formula IV) exhibit satisfactory u-v light stability even when the third position is occupied by Cl or Br. The u-v light stability of such compounds is enhanced by substituting any other substituent (Z) for the remaining Cl, which is effected without difficulty. Illustrative of compounds so formed are:

2-[(6-aminohexyl)amino]-4,6-bis[2,2,6,6-tetramethyl-4-piperidinyl[2-(3,3,5,5-tetramethyl-2-oxo-1-piperazinyl)ethyl]amino]-1,3,5-triazine;
2-piperidinyl-4,6-bis[2,2,6,6-tetramethyl-4-piperidinyl[2-(3,3,5,5-tetramethyl-2-oxo-1-piperazinyl)ethyl]amino]-1,3,5-triazine;
2-morpholinyl-4,6-bis[2,2,6,6-tetramethyl-4-piperidinyl[2-(3,3,5,5-tetramethyl-2-oxo-1-piperazinyl)ethyl]amino]-1,3,5-triazine; and,
2-cyclohexylamino-4,6-bis[2,2,6,6-tetramethyl-4-piperidinyl[2-(3,3,5,5-tetramethyl-2-oxo-1-piperazinyl)ethyl]amino]-1,3,5-triazine.

Illustrative of PIP-T compounds in which the triazine ring has two PSP substituents and a remaining Cl in the third position, and which are effective u-v light stabilizers are the following:

2-chloro-4,6-[1-methylpropyl[2-(3,3,5,5-tetramethyl-2-oxo-1-piperazinyl)ethyl]amino]-1,3,5-triazine;
2-chloro-4,6-[1,3-dimethylbutyl[2-(3,3,5,5-tetramethyl-2-oxo-1-piperazinyl)ethyl]amino]-1,3,5-triazine;
2-chloro-4,6-[cyclohexyl[(1-cyclohexyl-3,3,5,-trimethyl-2-oxo-1-piperazinyl)methyl]amino]-1,3,5-triazine; and,
2-chloro-4,6-bis-(isopropyl-[2-(3,3,5,5,-tetramethyl-2-oxo-1-piperazinyl]ethyl]amino]-1,3,5-triazine.

The foregoing reactions of a triazine compound with reactive functional groups and PSPs take place readily at the lower portion of the temperature range from about −10° C. to about 250° C. If a third PSP is to be introduced on to the triazine nucleus (as shown in structural formula III) the higher portion of the indicated temperature range will generally be found more suitable. Illustrative of PIP-T compounds in which three PSPs are distally linked to a triazine nucleus are the following:

2,4,6-tris[cyclohexyl[2-(3,3,5,5-tetramethyl-2-oxo-1-piperazinyl)ethyl]amino]1,3,5-triazine;
2,4,6-tris[N-(N-isopropyl-N-(2-(1,3,3,5,-tetramethyl-2-piperazinone)ethylamino)]-1,3,5-triazine;
2,4,6-tris[1-methylpropyl[2-(3,3,5,5-tetramethyl-2-oxo-1-piperazinyl)ethyl]amino]-1,3,5-triazine;
2,4,6-tris[1,3-dimethylbutyl[2-(3,3,5,5-tetramethyl-2-oxo-1-piperazinyl)ethyl]amino]-1,3,5-triazine; and,
2,4,6-tris[2,2,6,6-tetramethyl-4-piperidinyl[2-(3,3,5,5-tetramethyl-2-oxo-1-piperidinyl)ethyl]amino]-1,3,5-triazine.

Though it will also now be apparent that the primary purpose of preparing a 2AAD is to provide the necessary PSP substituent for the triazine ring and thus form the PIP-T compounds of this invention, it will be realized that numerous 2AAD compounds may be prepared with substituents which may have no especial importance relative to the efficacy of the u-v light stability of the eventual PIP-T stablizer compound, but which may have significance in other applications, and none of these 2AAD compounds could be prepared except by the selective reductive alkylation reaction described herein. These alkylated polyalkyleneamines are more particularly N-(alkyl)-N'-(aminoalkyl, or aminoaryl, or aminoaralkyl, or aminocycloalkyl)-1,-p-alkanediamines, wherein "p" refers to the number of methylene C atoms, which compounds have the structural formula

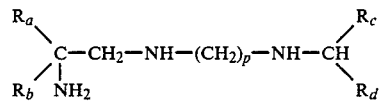

wherein,
$R_a$ and $R_b$ independently represent alkyl having from 1 to about 24 carbon atoms, aralkyl having from 7 to about 20 carbon atoms;
$R_a$ or $R_b$ may be cycloalkyl; or,
$R_a$ and $R_b$ together, when cyclized, may be cycloalkyl having from 5 to about 7 carbon atoms;
$R_c$ and $R_d$ independently represent alkyl having from 1 to about 24 carbon atoms, aralkyl having from 7 to about 20 carbon atoms;
$R_c$ or $R_d$ may be cycloalkyl; or,
$R_c$ and $R_d$ together, when cyclized, may be cycloalkyl having from 5 to about 7 carbon atoms; and,
represents an integer in the range from 2 to about 10.

Illustrative of 2AAD compounds which may be prepared by the reductive alkylation process of this invention are the following:

N-(2-propyl)-N'-(2-amino-2-ethylbutyl)1,2-ethanediamine;
N-cyclohexyl-N'-(2-amino-2-ethylbutyl)1,3-propanediamine;
N-(2-octyl)-N'-(2-amino-2-ethylbutyl)1,6-hexanediamine;
N-(2-propyl)-N'-(2-amino-2-2-diphenylethyl)-1,2-ethanediamine;
N-cyclohexyl-N'-(2-amino-2-2-diphenylethyl)-1,6-hexanediamine;
N-(2-propyl)-N'-(1-aminocyclohexylmethyl)-1,2-ethanediamine; and,
N-cyclohexyl-N'-(1-aminocyclohexylmethyl)-1,6-hexanediamine.

EXAMPLE 14

Preparation of 1-[3-(cyclohexylamino)propyl]-3,3,5,5-tetramethyl-2-piperazinone having the structural formula

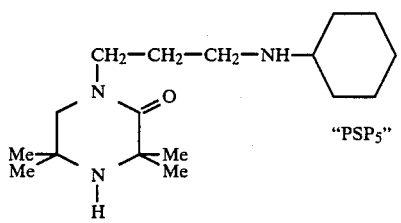

"PSP₅"

The above PSP₅ is prepared in a manner analogous to that described for the preparation of PSP₃ except that the starting material is N-cyclohexyl-N'-(2-amino-2-methylpropyl)-1,3-propanediamine.

EXAMPLE 15

Preparation of 1,1',1''-[1,3,5-triazine-2,4,6-triyl tris[(cyclohexylamino)-3,1-propanediyl]]tris[3,3,5,5-tetramethyl piperazinone] having the structure

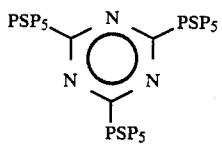

0.309 mole PSP5 is reacted with 0.103 mole cyanuric chloride in 450 ml xylene in the presence of 0.347 mole aqueous 20% NaOH solution in a 845 ml autoclave at 210° C. for about 16 hr. The product obtained has a mol wt of 961 and a m pt 182-189. In a test with 2 ml polypropylene tape in a manner analogous to that in which the tests reported in Table I were conducted, a test sample showed oven aging of more than 25 days, and Xenon Weather-O-Meter aging of more than 500 hr before and after extraction.

EXAMPLE 16

Preparation of poly[[6-(1,3-dimethyl-butyl[2-(3,3,5,5-tetramethyl-2-oxo-1-piperazinyl)ethyl]amino]-1,3,5-triazine-2,4-diyl]-1,4-piperazinediyl] having the structure

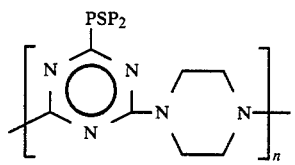

The above oligomer is prepared from 2,4-dichloro-6-[1,3-dimethyl-butyl[2-(3,3,5,5-tetramethyl-2-oxo-1-piperazinylethyl]amino]-1,3,5-triazine by reaction with piperazine.

The product obtained has a softening point 170° C. and $\overline{Mn}$2431. In a test with 2 ml polypropylene tape in a manner analogous to that in which the tests reported in Table I were conducted, a test sample showed oven aging of more than 25 days, and Xenon Weather-O-Meter aging of more than 500 hr before and after extraction.

EXAMPLE 17

Preparation of 1-[3-[[4-chloro-6-(cyclohexylamino)-1,3,5-triazine-2-yl]cyclohexylamino]propyl]-3,3,5,5-tetramethyl-piperazinone having the structure

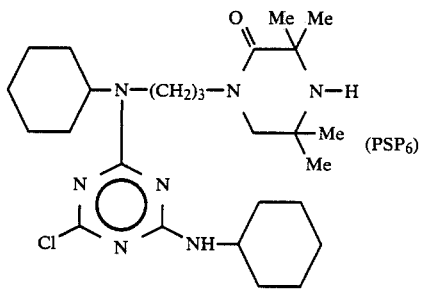

In a 500 ml three-necked flask was placed toluene and cooled to ice-bath temperature. Cyanuric chloride is added, then the amine solution, dropwise. This is followed by the addition of NaOH. When the first step is completed, cyclohexylamine is added, then more aqueous NaOH.

EXAMPLE 18

Preparation of 1,1'-[1,6-hexane-diyl bis[imino[6-cyclohexylamino)-1,3,5-triazine-4,2-diyl]cyclohexylimino)-3,1-propanediyl]]bis[3,3,5,5-tetramethylpieperazinone] having the structure

0.1 mole PSP6 is reacted with 0.05 mole 1,6-hexanediamine in a xylene solution in the presence of 20% aqueous NaOH. The product obtained has a mol wt 1054 and a m pt 101°-106° C. In a test with 2 ml polypropylene tape in a manner analogous to that in which the tests reported in Table I were conducted, a test sample showed oven aging of more than 25 days, and Xenon Weather-O-Meter aging of more than 500 hr before and after extraction.

EXAMPLE 19

Preparation of 1,1'-[1,4-piperazinediyl bis[[6-(cyclohexylamino)-1,3,5-triazine-4,2-diyl](cyclohexylimino)-3,1-propanediyl]]bis[3,3,5,5-tetramethylpiperazinone] have the structure

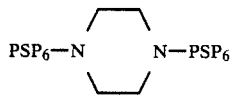

0.1 mole PSP6 is reacted with 0.05 mole piperazine in a xylene solution in the presence of 20% aqueous NaOH. The product obtained has a mol wt 1024 and a m pt 112°-118° C. In a test with 2 ml polypropylene tape in a manner analogous to that in which the tests reported in Table I were conducted, a test sample showed oven aging of more than 25 days, and Xenon Weather-O-Meter aging of more than 500 hr before and after extraction.

Though the linked piperazinone/triazine-containing compounds are excellent photostabilizers, they are also unexpectedly effective antioxidants. It was therefore all the more unexpected that, in combination with certain hindered phenols, these PIP-T compounds exhibit synergistic antioxidant and photostabilization activity. Only a phenol selected from the group consisting of tris(3,5-di-t-butyl-4-hydroxybenzyl)isocyanurate; 2,6-ditertiarylbutyl-p-cresol; 2,2'-ethylidenebis(4,6-ditertiarybutylphenol); and, octadecyl-3,5-di-t-butyl-4-hydroxybenzenepropionate exhibits such synergistic properties.

Such enhanced activity of the combination is particularly surprising since Cyasorb ® UV 3346, a commercially available triazinyl-piperidine made by American Cyanmid Company, does not exhibit such enhanced activity with the same hindered phenols. The structure of Cyasorb UV 3346 is hypothesized to be as follows:

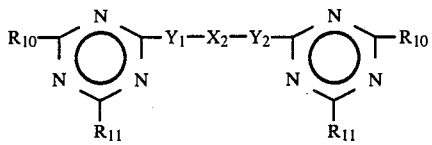

wherein
$R_{10}$ represents $C_3$–$C_6$ alkenyloxy; $C_3$–$C_6$ alkenylamino, or di($C_3$–$C_6$ alkenyl)amino;
$R_{11}$ represents $C_1$–$C_8$ alkyl, $C_1$–$C_8$ alkoxy, halo, $C_1$–$C_8$ alkylthio, $C_3$–$C_6$ alkenyloxy, amino, $C_3$–$C_6$ alkenylamino, di($C_3$–$C_6$ alkenyl)amino, and variously substituted piperidines;
$X_2$ represents alkylene, cycloalkylene, and variously substituted related compounds,
$Y_1$ and $Y_2$ represent oxy, and the like;
as set forth in greater detail in U.S. Pat. No. 4,400,505 the discloseu of which is incorporated by reference thereto as if fully set forth herein.

The activity of the combination of photostabilizer and antioxidant of this invention is also surprising since an oligomer having a triazine nucleus linked to pyrrolidone, piperidine and morpholine rings, and, a hindered phenol, do not show synergistic stabilization activity. Thus, an ineffective combination includes an oligomer which has the structure:

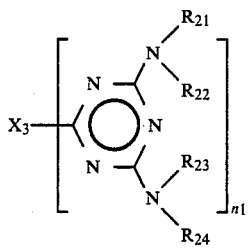

wherein,
$X_3$ is the amine residue obtained by removing one H atoms from each amino radical an alkylene diamine, alkylenepolyamine or saturated heterocyclic diamines containing $n_1$ primary amino radicals, which is connected with the C atoms of $n_1$ triazino radicals in each amino radical;
$R_{21}$ and $R_{23}$ are (un)saturated 1–18 C alkyl radicals, cycloalkyl, benzyl, methylbenzyl and halogenobenzyl radicals, 1–3 C cyanoalkyl radicals of 1–3 C (sic), hydroxyalkyl and dimethylamino radicals of 2 or 3 C (sic);
$R_{22}$ and $R_{24}$ are H or the same radicals as given for $R_{21}$ and $R_{23}$, provided that only when $R_{22}$ or $R_{24}$ is H, can $R_{21}$ or $R_{23}$ be dimethylamino; also $R_{21-24}$ may represent ethyleneimino, pyrrolidno, piperidino, or morpholino heterocyclic rings containing 2–5 carbon atoms with $R_{21}$ and $R_{22}$, or $R_{23}$ and $R_{24}$ combined to each other;
and, $n_1$ is an integer in the range from 2 to 5;
as set forth in greater detail in Japanese Pat. No. J 1004-247, the disclosure of which is incorporated by reference thereto as if fully set forth herein.

The activity of the combination of PIP-T and hindered phenol stabilizers is also surprising in view of the ineffectiveness of another piperidyl-triazine derivative such as Chimassorb 944 and one of the hindered phenols of our combination. Such piperidyl-triazine compounds have the structure:

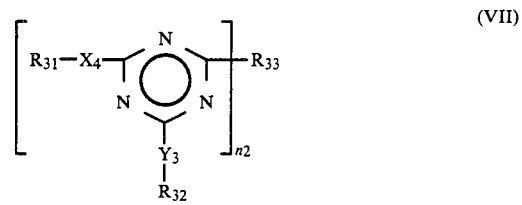 (VII)

wherein,
$R_{31}$, $R_{32}$, same or different, are straight or branched chain $C_1$ to $C_{18}$ alkyl, $C_5$ to $C_{18}$ cycloalkyl, $C_6$ to $C_{18}$ aryl, $C_7$ to $C_{18}$ aralkyl or a piperidine radical having the formula

 (VIII)

in which $R_{34}$, $R_{35}$, $R_{37}$, $R_{38}$, same or different, are selected from $C_1$ to $C_6$ alkyl and $R_{36}$ is selected from H, O, $C_1$ to $C_{12}$ alkyl, $C_2$ to $C_{12}$ alkenyl or alkinyl,
a group

in which $R_{39}$, $R_{40}$, same or different, are selected from H, a $C_1$ to $C_8$ alkyl, a $C_5$ to $C_8$ cycloalkyl or a $C_6$ to $C_8$ aryl;
$X_4$, $Y_3$, same or different, are —O—, —S—, or

$R_{41}$ being selected from H, a straight or branched $C_1$ to $C_{18}$ alkyl, $C_5$ to $C_{18}$ cycloalkyl, $C_6$ to $C_{18}$ aryl, $C_7$ to $C_{18}$ aralkyl, or a piperidine radical having said formula (VIII); and, when $X_4$ or $Y_2$ is

the radicals attached thereto can also be H;

the radicals $R_{31}$—$X_4$—, $R_{32}$—$Y_2$, taken as a single substituent group representing a radical of a nitrogenous heterocyclic compound having 5 to 8 atoms linked to the triazine ring by means of a disubstituted nitrogen atom of said radical, as well as representing Cl- and Br-;

$n_2$ is an integer from 2 to 6;

$R_{33}$ is an $n_2$-valent residue derived from a polyalcohol, a polymercaptan, or a polyamine by reaction of the active H atoms thereof with a halogen atom of a monohalogen triazine;

in the formula (VII) there is in at least one of the radicals $R_{31}$—$X_4$—, $R_{32}$—$Y_3$—, $R_{33}$, at least one piperidine radical of the formula (VIII) present;

as set forth in greater detail in U.S. Pat. No. 4,108,829 the disclosure of which is incorporated by reference thereto as if fully set forth herein.

The foregoing combination of a PIP-T compound of this invention, in particular, and a designated hindered phenol may be used in any of the polymers specified hereinbefore, but they are most preferably used in a polyolefin which is a normally solid homopolymer, copolymer or terpolymer of aliphatic 1-olefins having from 2 to 10 carbon atoms molecule, and blends thereof. Specific examples include polyethylene, polypropylene, poly(1-butene), copolymers of ethylene/propylene, ethylene/1-hexane, ethylene/1-decene, propylene/ethylene/1-butene, and the like. Presently preferred polymers include propylene and propylene/1-olefin copolymers containing at least 90 mole % propylene and from about 0.1 to about 10 mole % of a 1-olefin comonomer, particularly ethylene, made by conventional processes.

In addition to the particular PIP-T compound of this invention, used in the amount specified hereinabove, the amount of hindered phenol used is preferably in the range from about 0.01 part to about 5 parts by weight, per 100 parts of the polymeric composition, though in many instances larger amounts may be used without substantially adversely affecting the physical characteristics of the polymer, if economics justify the use of such larger amounts.

The following results are illustrative of the synergistic properties of particular combinations of PIP-T compound and specified phenols.

The photostabilization tests in the Xenon Weather-O-Meter were carried out as described hereinbefore to determine the number of hours after which tensile strength left was 50% of strength before exposure.

The thermal oxidation tests were carried out in a convection oven, in the presence of air, using plaques of Profax 6501 polypropylene containing specified concentrations of stabilizers. Each plaque was 1"×1"×0.020". All tests were carried out in triplicate, the plaques being suspended in the test apparatus. At periodic intervals, the condition of the plaques was examined. A plaque was deemed degraded to the point of failure when it crumbled when pressed between a finger and thumb.

In the following Table II the concentration of each stabilizer used is 0.125 phr, and as will be evident, such amount is sufficient to slow the rate of degradation due to light and thermal oxidation.

Commercial and code names are used to identify the stabilizers, for convenience and easy recognition.

TABLE II

| Stabilizer(s) used | Degradation to Failure | | | |
|---|---|---|---|---|
| | Oven aging (days) | | +WeatherOmeter (hr) | |
| | T.A.E.* | Actual | T.A.E.* | Actual |
| Profax 6501 blank (no additives) | | 2 | | 140 |
| Compound 8(A) | | 58 | | 820 |
| Chimassorb 944 | | 40 | | 940 |
| Goodrite 3114 | | 50 | | 420 |
| Chimassorb 944 + Goodrite 3114 | 90 | 80 | 1360 | 1010 |
| Compound 8(A) + Goodrite 3114 | 108 | 176 | 1240 | 1940 |
| Isonox 129 | | 37 | | 320 |
| Chimassorb 944 + Isonox 129 | 77 | | 1260 | |
| Compound 8(A) + Isonox 129 | 95 | 164 | 960 | 1760 |
| BHT | | 40 | | 280 |
| Chimassorb 944 + BHT | 80 | | 1220 | |
| Compound 8(A) + BHT | 98 | 140 | 1100 | 1660 |
| Irganox 1076 | | 40 | | 320 |
| Chimassorb 944 + Irganox 1076 | 80 | | 1260 | |
| Compound 8(A) + Irganox 1076 | 98 | 140 | 1140 | 1260 |
| Compound 7(C) | | 65 | | 1220 |
| Compound 7(C) + Goodrite 3114 | 115 | 188 | 1640 | 2230 |
| Compound 7(C) + Isonox 129 | 87 | 160 | 1540 | 1640 |
| Compound 7(C) + BHT | 90 | 154 | 1500 | 1820 |
| Compound 7(C) + Irganox 1076 | 90 | 140 | 1540 | 1680 |
| Cyasorb UV3346 | | 40 | | 920 |
| Cyasorb UV3346 + Goodrite 3114 | 90 | 110 | 1340 | 1320 |
| Cyasorb UV3346 + Isonox 129 | 77 | 80 | 1240 | 1260 |
| Cyasorb UV3346 + BHT | 80 | 85 | 1200 | 1160 |
| Cyasorb UV3346 + Irganox 1076 | 120 | 115 | 1240 | 1200 |

*T.A.E. = Theoretical Additive Effect
+WeatherOmeter plaques were 1" × 1" × 0.002"

We claim:

1. An improved photostabilizer and antioxidant composition, for slowing the rate of degradation of degradable synthetic resinous material subject to ultraviolet light degradation and thermal oxidation, comprising (a) from about 0.1 part to about 5 parts by weight of a stabilizer compound (designated "PIP-T") having a polysubstitued piperazinone ring linked to a triazine ring, and, (b) from about 0.1 part to about 5 parts by weight of a hindered phenol selected from the group consisting of tris(3,5-di-t-butyl-4-hydroxybenzyl)isocyanurate; 2,6-ditertiarylbutyl-p-cresol; 2,2'-ethylidenebis(4,6-ditertiarybutylphenol); and, octadecyl-3,5-di-t-butyl-4-hydroxybenzenepropionate.

2. The composition of claim 1 wherein said PIP-T is represented by the structural formula

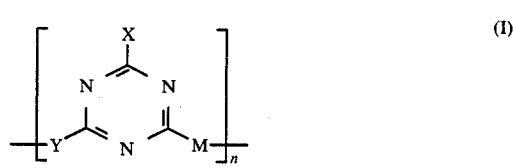

(I)

wherein, n is an integer in the range from 1 to about 10, said compound having functional end groups selected from H, OH and Cl when n is greater than 1;

X is a substituent having the following formula (II):

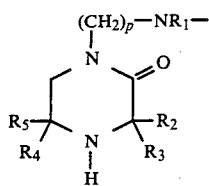

wherein,
- R₁ represents alkyl having from 1 to about 24 carbon atoms, cycloalkyl having from 5 to about 7 carbon atoms, aralkyl having from 7 to about 20 carbon atoms, azaalkyl having from 1 to about 24 carbon atoms, and azacycloalkyl having from 6 to about 20 carbon atoms;
- R₂, R₃, R₄ and R₅ independently represent alkyl having from 1 to about 24 carbon atoms;
- p represents an integer in the range of from 2 to about 10;
- Y may be the same as X or M;
- M may be Z or Z', wherein
- Z represents a radical selected from the group consisting of

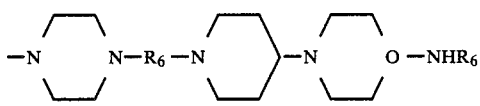

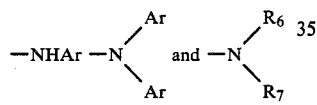

Ar=aryl, aralkyl, phenyl
R₆, R₇ represent alkyl having from 2 to about 24 carbon atoms;
Ar represents aryl, aralkyl, and phenyl;
Z' represents a radical selected from the group consisting of

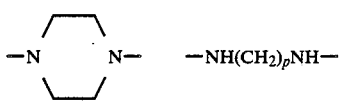

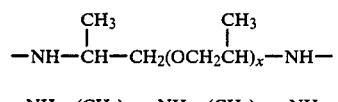

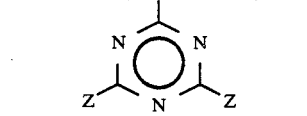

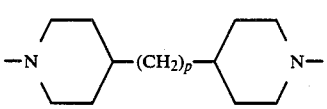

-continued

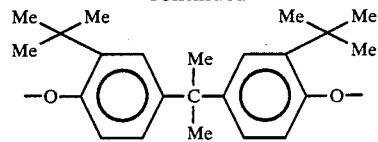

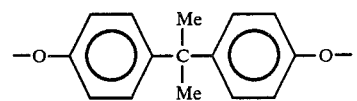

Me=methyl
x represents an integer in the range from 1 to about 50; and, when n=1, Y and M may be the same as X, and,
Z and X' each includes a terminal functional group selected from H, lower alkyl having from 1 to about 5 carbon atoms, and hydroxyalkyl having from 1 to about 5 carbon atoms.

3. The composition of claim 2 wherein said stabilizer compound has the structural formula

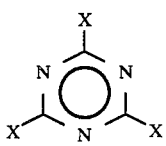

(III)

4. The composition of claim 2 wherein said stabilizer compound has the structural formula

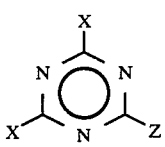

(IV)

5. The composition of claim 2 wherein said stabilizer compound has the structural formula

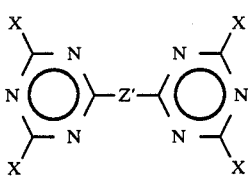

(V)

6. The composition of claim 2 wherein said stabilizer compound has the structural formula

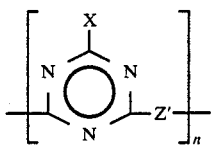

(VI)

7. The composition of claim 2 wherein said stabilizer compound is selected from the group consisting of:
2,4-bis(1-piperidinyl)-6-[1-methylpropyl[2-(3,3,5,5-tetramethyl-2-oxo-1-piperazinyl)ethyl]amino]-1,3,5-triazine;

2,4-bis(1-piperidinyl)-6-[(1,3-dimethylbutyl[2-(3,3,5,5-tetramethyl-2-oxo-1-piperazinyl)ethyl]amino]-1,3,5-triazine;

2,4-bis(1-piperidinyl)-6-[cyclohexyl[2-(3,3,5,5-tetramethyl-2-oxo-1-piperazinyl)ethyl]amino]-1,3,5-triazine, and, 2,4-bis(4-morpholinyl)-6-[cyclohexyl[2-(3,3,5,5-tetramethyl-2-oxo-1-piperazinyl)ethyl]amino]-1,3,5-triazine.

8. The composition of claim 2 wherein NR$_8$ represents an amine, wherein R$_8$ is selected from the group consisting of alkyl having from 1 to about 24 carbon atoms, cycloalkyl having from 5 to about 7 carbon atoms, phenyl, and aralkyl having from 7 to about 20 carbons atoms so that NR$_8$ is represented by the structure

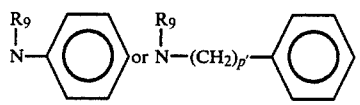

wherein R$_9$ is alkyl, and the combined number of alkyl carbon atoms and alkylene carbon atoms p' is in the range from 1 to 14.

9. The composition of claim 3 wherein said stabilizer compound is selected from the group consisting of:
2,4,6-tris[cyclohexyl[2-(3,3,5,5-tetramethyl-2-oxo-1-piperazinyl)ethyl]amino]1,3,5-triazine;
2,4,6-tris[N-(N-isopropyl-N-(2-(1-3,3,5,-tetramethyl-2-piperazinone)ethylamino)]-1,3,5-triazine;
2,4,6-tris[1-methylpropyl[2-(3,3,5,5-tetramethyl-2-oxo-1-piperazinyl)ethyl]amino]-1,3,5-triazine;
2,4,6-tris[1,3-dimethylbutyl[2-(2,3,5,5-tetramethyl-2-oxo-1-piperazinyl)ethyl]amino]-1,3,5-triazine; and,
2,4,6-tris[2,2,6,6-tetramethyl-4-piperidinyl[2-(3,3,5,5-tetramethyl-2-oxo-1-piperidinyl)ethyl]amino]-1,3,5-triazine.

10. The composition of claim 4 wherein said stabilizer compound is selected from the group consisting of:
2-chloro-4,6-[1-methylpropyl[2-(3,3,5,5-tetramethyl-2-oxo-1-piperazinyl)ethyl]amino]-1,3,5-triazine;
2-chloro-4,6-[1,3-dimethylbutyl[2-(3,3,5,5-tetramethyl-2-oxo-1-piperazinyl)ethyl]amino]-1,3,5-triazine;
2-chloro-4,6-[cyclohexyl[(1-cyclohexyl-3,3,5,-trimethyl-2-oxo-1-piperazinyl)methyl]amino]-1,3,5-triazine;
2-chloro-4,6-bis-(isopropyl-[2-(3,3,3,5,-tetramethyl-2-oxo-1-piperazinyl]ethyl]amino]-1,3,5-triazine;
2-[(6-aminohexyl)amino]-4,6-bis[2,2,6,6-tetramethyl-4-piperidinyl[2-(3,3,5,5-tetramethyl-2-oxo-1-piperazinyl)ethyl]amino]-1,3,5-triazine; and,
1,1',1''-[1,3,5-triazine-2,4,6-triyl tris[(cyclohexylamino)-3.1-propanediyl]]tris[3,3,5,5-tetramethyl piperazinone].

11. The composition of claim 5 wherein said stabilizer compound is selected from the group consisting of:
1,1',1'',1'''-[1,4-piperazinyl-1,3,5-triazine-6,2,4-triylbis[[iso-propylamino]-2,1-ethanediyl]]]tetrakis[3,3,5,5-tetramethylpiperazinone];
1,1',1'',1'''-[1,3-propanediylbis[4,1-piperidinyl--1,3,5-triazine-6,2,4-triylbis[[(cyclohexyl-)imino]2,1-ethanediyl]]]tetrakis[3,3,5,5-tetramethylpiperazinone];
1,1',1'',1'''-[1,4-piperazinyl-1,3,5-triazine-6,2,4-triylbis[[(cyclohexyl)imino]-2,1-ethanediyl]]]tetrakis[3,3,5,5-tetramethylpiperazinone];
1,1'-[[6-[4-[2-[4,6-bis[cyclohexyl[2-(3,3,5,5-tetramethyl-2-oxo-1-piperazinyl)ethyl]amino]-1,3,5-triazine-2-yl]amino]ethyl]1-piperazinyl]-1,3,5-triazin-2,4-diyl]bis[cyclohexyl-imino-2,1-ethane-diyl]-bis[3,3,5,5-tetramethylpiperazinone];
1,1',1'',1'''-[1,6-hexanediylbis[imino-1,3,5-triazine-6,2,4-triylbis[[(2,2,6,6-tetramethyl-4-piperidinyl)imino]-2,1-ethanediyl]]]tetrakis[3,3,5,5-tetramethylpiperazinone];
1,1'-[1,6-hexane-diyl bis[imino[6-cyclohexylamino)-1,3,5-triazine-4,2-diyl]cyclohexylimino)-3,1-propanediyl]]bis[3,3,5,5-tetramethylpieperazinone]; and,
1,1'-[1,4-piperazinediyl bis[[6-(cyclohexylamino)-1,3,5-triazine-4,2-diyl](cyclohexylimino)-3,1-propanediyl]]bis[3,3,5,5-tetramethylpiperazinone].

12. The composition of claim 6 wherein said stabilizer compound is selected from the group consisting of:
poly[[6-[1-methylpropyl[2-(3,3,5,5-tetramethyl-2-oxo-1-piperazinyl)ethyl]amino]-1,3,5-triazine-2,4-diyl]imino-1,6-hexanediylimino];
poly[[6-[1-methylpropyl[2-(3,3,5,5-tetramethyl-2-oxo-1-piperazinyl)-ethyl]amino]-1,3,5-triazine-2,4-diyl]oxy-1,4-phenylene(1-methylethylidene)-1,4-phenyleneoxy];
poly[[6-[1-methylpropyl[2-(3,3,5,5-tetramethyl-2-oxo-1-piperazinyl)ethyl]amino]-1,3,5-triazine-2,4-diyl]imino-1,4-cyclohexanediylmethylene-1,4-cyclohexanediylimino];
poly[[6-[1-methylpropyl[2-(3,3,5,5-tetramethyl-2-oxo-1-piperazinyl)ethylamino]-1,3,5-triazine-2,4-diyl]imino-1,2-ethanediylimino];
poly[[6-[1-methylpropyl[2-(3,3,5,5-tetramethyl-2-oxo-1-piperazinyl)ethyl]amino]-1,3,5-triazine-2,4-diyl]-1,4-piperazinediyl];
poly[[6-[1-methylpropyl[2-(3,3,5,5-tetramethyl-2-oxo-1-piperazinyl)ethyl]amino]-1,3,5-triazine-2,4-diyl]imino-1,2-cyclohexanediyl imino];
poly[[6-[1,3-dimethylbutyl[2-(3,3,5,5-tetramethyl-2-oxo-1-piperazinyl)ethyl]amino]-1,3,5-triazine-2,4-diyl]imino-1,6-hexanediylimine];
poly[[6-[1,3-dimethylbutyl[2-(3,3,5,5-tetramethyl-2-oxo-1-piperazinyl)ethyl]amino]-1,3,5-triazine-2,4-diyl]oxy-1,4-phenylene(1-methylethylidene)-1,4-phenyleneoxy];
poly[[6-[1,3-dimethylbutyl[2-(3,3,5,5-tetramethyl-2-oxo-1-piperazinyl)ethyl]amino]-1,3,5-triazine-2,4-diyl]imino-1,4-cyclohexanediylmethylene-1,4-cyclohexanediylimino];
poly[[6-[1,3-dimethylbutyl[2-(3,3,5,5-tetramethyl-2-oxo-1-piperazinyl)ethyl]amino]-1,3,5-triazine-2,4-diyl]imino-1,2-ethanediylimino];
poly[[6-[1,3-dimethylbutyl[2-(3,3,5,5-tetramethyl-2-oxo-1-piperazinyl)ethyl]amino]-1,3,5-triazine-2,4-diyl]-1,4-piperazinediyl];
poly[[6-[1,3-dimethylbutyl[2-(3,3,5,5-tetramethyl-2-oxo-1-piperazinyl)ethyl]amino]-1,3,5-triazine-2,4-diyl]imino-1,2-cyclohexanediylimino];
poly[[6-cyclohexyl[(1-cyclohexyl-(3,3,5,5-tetramethyl-2-oxo-5-piperazinyl)methyl]amino]-1,3,5-triazine-2,4-diyl]imino-1,6-hexanediylimino];
poly[[6-[cyclohexyl[2-(3,3,5,5-tetramethyl-2-oxo-1-piperazinyl)ethyl]amino]-1,3,5-triazine-2,4-diyl]oxy-1,4-phenylene(1-methylidene)-1,4-phenyleneoxy];
poly[[6-[cyclohexyl[2-(3,3,5,5-tetramethyl-2-oxo-1-piperazinyl)ethyl]amino]-1,3,5-triazine-2,4-diyl- ]imino-1,4-cyclohexanediylmethylene-1,4-cyclohexanediylimino];

poly[[6-[cyclohexyl[(1-cyclohexyl-3,3,5-trimethyl-2-oxo-5-piperazinyl)methyl]amino]-1,3,5-triazine-2,4-diyl]-1,4-piperazinediyl];

poly[[6-[cyclohexyl[(1-cyclohexyl-3,3,5-trimethyl-2-oxo-5-piperazinyl)methyl]amino]-1,3,5-triazine-2,4-diyl]imino-1,2-cyclohexanediylimino];

poly[[6-[cyclohexyl[2-(3,3,5,5-tetramethyl-2-oxo-1--piperazinyl)ethyl]amino]-1,3,5-triazine-2,4-diyl]oxy-1,4-[2-(1,1-dimethylethyl)]phenylene(1-methylethylidene)-1,4-[3-(1,1-dimethylethyl)]phenyleneoxy];

poly[[6-[cyclohexyl[2-(3,3,5,5-tetramethyl-2-oxo-5-piperazinyl)ethyl]amino]-1,3,5-triazine-2,4-diyl]imino-1,2-ethanediyl-1,4-piperazinediyl];

poly[[6-[cyclohexyl[2-(3,3,5,5-tetramethyl-2-oxo-1-piperazinyl)ethyl]amino]-1,3,5-triazine-2,4-diyl]imino-1,3-propanediyl-1,4-pipeazinediyl-1,3-propanediylimino];

poly[[6-[cyclohexyl[1-cyclohexyl-3,3,5-trimethyl-2-oxo-5-piperazinyl)methyl]amino]-1,3,5-triazine-2,4-diyl]imino-1,2-ethanediyl-1,4-piperazinediyl]; and, poly[[6-(1,3-dimethyl-butyl[2-(3,3,5,5-tetramethyl-2-oxo-1-piperazinyl)ethyl]amino]-1,3,5-triazine-2,4-diyl]-1,4-piperazinediyl].

* * * * *